(12) United States Patent
Higuchi

(10) Patent No.: US 7,218,961 B2
(45) Date of Patent: May 15, 2007

(54) PERCENT BODY FAT MEASURING APPARATUS USING A HALF-WAVE WAVEFORM

(75) Inventor: Yoshio Higuchi, Osaka (JP)

(73) Assignee: Funai Electric Co., Ltd., Daito-shi (JP)

( * ) Notice: Subject to any disclaimer, the term of this patent is extended or adjusted under 35 U.S.C. 154(b) by 657 days.

(21) Appl. No.: 10/390,976

(22) Filed: Mar. 18, 2003

(65) Prior Publication Data

US 2004/0127811 A1   Jul. 1, 2004

(30) Foreign Application Priority Data

Mar. 19, 2002   (JP)   .......................... P 2002-075680
Mar. 26, 2002   (JP)   .......................... P 2002-084807

(51) Int. Cl.
*A61B 5/05* (2006.01)
(52) U.S. Cl. ..................................... 600/547
(58) Field of Classification Search ................ 600/547, 600/554, 506, 536; 324/692
See application file for complete search history.

(56) References Cited

U.S. PATENT DOCUMENTS

| | | | | |
|---|---|---|---|---|
| 3,557,625 A | * | 1/1971 | Leger, Jr. et al. | 73/866 |
| 4,895,163 A | * | 1/1990 | Libke et al. | 600/547 |
| 4,947,862 A | * | 8/1990 | Kelly | 600/547 |
| 5,372,141 A | * | 12/1994 | Gallup et al. | 600/547 |
| 5,611,351 A | * | 3/1997 | Sato et al. | 600/547 |
| 6,011,992 A | * | 1/2000 | Hubbard et al. | 600/547 |
| 6,208,890 B1 | * | 3/2001 | Sarrazin et al. | 600/547 |
| 6,370,425 B1 | * | 4/2002 | Oguma | 600/547 |
| 6,509,748 B1 | * | 1/2003 | Cheng | 324/696 |

FOREIGN PATENT DOCUMENTS

| | | | |
|---|---|---|---|
| JP | 2835656 | | 10/1998 |
| JP | 11-104104 | | 4/1999 |
| JP | 11-113872 | | 4/1999 |
| JP | 2001-37735 A | * | 2/2001 |
| JP | 2001-212098 | | 8/2001 |

* cited by examiner

Primary Examiner—Max Hindenburg
Assistant Examiner—Michael Apanius
(74) Attorney, Agent, or Firm—Osha Liang LLP

(57) ABSTRACT

A percent body fat measuring apparatus includes a first and a second electrodes with which a living body is brought into contact, a detection resistor of which one terminal is connected to the second electrode, signal generator which produces a measurement signal and applies a produced measurement signal between the first electrode and the other terminal of the detection resistor, level detector for detecting the level of a signal which develops between the terminals of the detection resistor and is an object of detection, and percent body fat computer for determining percent body fat on the basis of a result of detection operation performed by the level detector. A measurement signal produced by the signal generator is made analogous to a half-wave waveform, and the level detector detects the level of a waveform analogous to a half-wave of the signal to be detected.

10 Claims, 16 Drawing Sheets

PERCENT BODY FAT MEASURING APPARATUS USING A HALF-WAVE WAVEFORM

BACKGROUND OF THE INVENTION

The invention relates to a percent body fat measuring apparatus for measuring percent body fat on the basis of bio-impedance, and more particularly, to a percent body fat measuring apparatus which measures bio-impedance by causing a signal analogous to a half-wave waveform to flow through a living body.

As described in, e.g., the Japanese Patent No. 2835656, the Unexamined Japanese Patent Application Publication Nos. Heill-104104, Heill-113872, and 2001-212098, according to related-art techniques for measuring bio-impedance, a sinusoidal waveform of 50 KHz or the like is used as a measurement signal to be caused to flow through a living body (hereinafter called a "measurement signal"). A voltage stemming from flow of the measurement signal through the living body is extracted through use of an electrode to be brought into contact with the living body. Next, after being amplified by a differential amplifier, the voltage is converted into a d.c. voltage through use of a rectifier circuit. A d.c. level of the voltage is read through use of an analog-to-digital converter (this technique is taken as a first "related-art").

Under the assumption that a circuit shown in FIG. 15 is used as the rectifier circuit, when a voltage of operating power is set to, e.g., four volts, a range of variation in the level of a rectified output assumes a value of about 1.5 volts, because of influence of a forward voltage of a diode which performs rectification. Specifically, this results in occurrence of a deficiency in the rectified output. With a view toward eliminating such a problem, a circuit shown in FIG. 13 is put forth. Specifically, a scan be seen from an input and an output of the circuit shown in the drawing, when an input varies from zero volts to two volts, an output varies from four volts to two volts. Accordingly, when the voltage of the operating power is set to four volts, the range of variation in the level of the rectified output can be set to two volts. Specifically, the circuit prevents narrowing of the range of variation in the level of the rectified output, which would otherwise be caused under the influence of the forward voltage of the diode which performs rectifying operation (this technique is taken as a second related-art technique).

Further, when bio-impedance is measured, a measurement signal, such as an a.c. signal, is caused to flow through a living body, and a voltage stemming from flow of the measurement signal through the living body is detected. However, the thus-detected voltage sustains the influence of an error of a value of the electric current flowing through the living body or the influence of an error arising in a detection circuit for detecting a voltage. A related-art technique for solving such an error is put forward in Japanese Patent No. 2835656. According to this technique, a plurality of groups of reference resistors are inserted in current paths which permit flow of the measurement signal into the living body. Voltage drop values corresponding to the respective reference resistors, which differ in resistance value from each other, and a voltage drop value corresponding to the living body are measured through use of a single circuit under the same measurement environment. From the values of the respective reference resistors and the voltage drop values corresponding to the respective reference resistors, a correlation between a voltage drop value and impedance is determined. The thus-determined correlation is applied to a voltage drop value of the living body, to thereby compute bio-impedance. The error of the value of the electric current flowing through the living body and the error arising in the detection circuit for detecting a voltage are eliminated. Consequently, the thus-measured bio-impedance assumes a highly accurate value (this technique is taken as a first related-art technique).

A configuration shown in FIG. 21 is also put forward, by the present applicant. More specifically, signal generator 503 for producing a measurement signal whose waveform is analogous to a half-wave waveform is provided, and a generated measurement signal is applied to a first electrode 501. A second electrode 502 is grounded by way of a detection resistor R514. The level of a half-wave of a half-wave signal developing between terminals of the detection resistor R514 is detected by use of level detector 504. The level detector 504 is configured from only discrete elements which are inexpensive (this technique is taken as a second related-art technique).

As is touched on in the description of the second related-art technique, the voltage of the operating power for an apparatus which displays percent body fat on the basis of measured bio-impedance (i.e., a percent body fat measuring apparatus) is set to a low voltage such as four volts. In order to facilitate transport of the apparatus, a battery is used as a power source. According to the first related-art technique, an amplitude of the measurement signal is limited to a value as low as four volts. In contrast, a signal detected from the living body is rectified after being amplified. Specifically, only a half-wave component of the sinusoidal wave becomes effective for measuring bio-impedance. Put another way, even when the operating power is set to four volts and when the amplitude of the measurement signal is also set to four volts, only a component corresponding to two volts is utilized as an effective component. As described in connection with the second related-art technique, a rectifier circuit formed from a complicated circuit configuration is required. Even when a rectifier circuit having such a complicated circuit configuration is used, the range of variation in the rectified output is limited to two volts. Therefore, when the level of a signal developing in the living body as a result of flow of the measurement signal through the living body is detected, difficulty is encountered in improving a detection accuracy.

Further, according to the second related-art technique, when a temperature rises, a base current of a p-n-p transistor Q501 also increases. Hence, an output level of the collector of the transistor rises in association with the temperature rise. A forward voltage of a diode D506 decreases in association with the temperature rise. Even when the level of the collector remains constant, a rectified output 651 is increased in response to the temperature rise. Consequently, as a whole, the temperature change induces occurrence of synergistic action between an increase in the base current of the p-n-p transistor Q501 and a decrease in the forward voltage of the diode D506, thereby deteriorating a temperature characteristic. According to the second related-art technique having such a characteristic, the level of the signal developing between the terminals of the detection resistor R514 directly indicates bio-impedance Z to be measured. Hence, the method for eliminating an error according to the first related-art technique cannot be applied to the second related-art technique. Therefore, demand arises for another method for enhancing accuracy of detection of the bio-impedance Z.

SUMMARY OF THE INVENTION

The invention is conceived to solve the problem and is aimed at providing a percent body fat measuring apparatus which enables enhancement of measurement accuracy required when the level of a signal detected through use of electrodes is measured, generation of a measurement signal analogous to a half-wave waveform through use of a simple circuit configuration, conversion of the signal detected through use of the electrodes into a d.c. signal through use of a simple circuit configuration, and prevention of occurrence of a variation in the waveform of the measurement signal even when a variation has arisen in power voltage of a microcomputer which produces a pulse signal representing the cycle of the measurement signal.

The invention is also aimed at providing a percent body fat measuring apparatus which enables enhancement of measurement accuracy required when the level of a signal detected through use of electrodes is measured by making the waveform of a measurement signal analogous to a half-wave waveform, to thereby render the level of a rectified output similar to the amplitude of a signal before rectification.

In addition to achieving the foregoing objects, the invention also provides a percent body fat measuring apparatus which enables generation of a measurement signal analogous to a half-wave waveform through use of a simple circuit configuration and without use of an operation amplifier having a complicated equivalent circuit configuration.

In addition to achieving the foregoing objects, the invention also provides a percent body fat measuring apparatus which enables conversion of a signal detected through use of electrodes into a d.c. signal with a simple circuit configuration and without use of an operation amplifier having a complicated equivalent circuit configuration.

In addition to achieving the foregoing objects, the invention also provides a percent body fat measuring apparatus capable of preventing occurrence of a variation in the waveform of a measurement signal even when a variation arises in a power voltage of a microcomputer which generates a pulse signal representing the cycle of a measurement signal.

Further, the invention is conceived to solve the problem and is aimed at providing a percent body fat measuring apparatus which enables simplification of a computation program for preventing occurrence of a drop in measurement accuracy of percent body fat ratio, which would otherwise be caused by a temperature change, and for enhancing the measurement accuracy.

The invention is aimed at providing a percent body fat measuring apparatus which corrects an output level of level detector to be obtained at the time of measurement, through use of an output level achieved when an operating point is forcefully shifted and which prevents a decrease in measurement accuracy of percent body fat, which would otherwise be caused by a temperature change, by determining percent body fat on the basis of a correction result.

To solve the problem, the invention provides a percent body fat measuring apparatus including;

first and second electrodes with which a living body is brought into contact;

a detection resistor of which one terminal is connected to the second electrode;

signal generator which produces a measurement signal and applies a produced measurement signal between the first electrode and the other terminal of the detection resistor;

level detector for detecting the level of a signal which develops between the terminals of the detection resistor and is an object of detection; and percent body fat computer for determining percent body fat on the basis of a result of detection operation performed by the level detector, wherein a measurement signal produced by the signal generator is made analogous to a half-wave waveform;

the level detector detects the level of a waveform analogous to a half-wave of the signal to be detected;

the signal generator has;

pulse generator for generating a pulse signal indicating the cycle of the measurement signal, a first resistor of which one terminal is connected to an output terminal of the pulse generator, a second resistor of which one terminal is connected to the other terminal of the first resistor, a first p-n-p transistor of which base is connected to the other terminal of the second resistor, of which collector is grounded, and of which emitter is connected to a positive power supply via a third resistor, a first capacitor of which one terminal is connected to a node between the first and second resistors and of which other terminal is connected to the emitter of the first p-n-p transistor, and a second capacitor connected between a base of the first p-n-p transistor and a ground level;

the level detector has;

a third capacitor of which one terminal is connected to the second electrode, a second p-n-p transistor of which base is connected to the other terminal of the third capacitor, of which collector is grounded via a fourth resistor, and of which emitter is connected to the positive power supply via a fifth resistor, a bias circuit for supplying a bias current to the base of the second p-n-p transistor, and a rectifier circuit for rectifying an output from the collector of the second p-n-p transistor;

the pulse generator has;

original pulse generator which is formed from a microcomputer and produces an original pulse signal indicating the cycle of the measurement signal, a sixth resistor of which one terminal is connected to the positive power supply, and a switching element of which one terminal is connected to the other terminal of the sixth resistor, of which other terminal is grounded, and whose connection is controlled by the original pulse signal; and a node between the sixth resistor and the switching element is taken as a terminal for outputting the pulse signal.

The measurement signal is analogous to a half-wave waveform. Hence, when the level detector detects the level of a waveform analogous to a half-wave, the thus-detected level is substantially equal to the amplitude of a signal before rectification. Specifically, as in the case of use of a sinusoidal waveform, the level of a rectified signal is prevented from being reduced to one-half the amplitude of the signal before rectification. Moreover, a time constant determined by the first resistor and the first capacitor is set to a value close to one-half the cycle of the pulse signal. Further, a time constant determined by the second resistor and the second capacitor is sufficiently made smaller than the time constant determined by the first resistor and the first capacitor. In this case, a waveform analogous to a half-wave waveform appears on the emitter of the first p-n-p transistor during durations before and after a rising edge of a pulse signal. The signal generator for producing a half-wave waveform is formed from a small number of elements other than the pulse generator; that is, three resistors, two capacitors, and one p-n-p transistor. Further, the bias circuit can be formed from two resistors. The rectifier circuit can be formed from one diode, one resistor, and one capacitor. Accordingly, the level detector can be formed from a small number of elements; that is, five resistors, two capacitors, one p-n-p transistor, and one diode. Even when variations arise in the voltage of operating power supplied to the microcomputer, a high-level voltage of the pulse signal to be output remains constant at all times.

The invention also provides a percent body fat measuring apparatus including;

first and second electrodes with which a living body is brought into contact;

a detection resistor of which one terminal is connected to the second electrode;

signal generator which produces a measurement signal and applies a produced measurement signal between the first electrode and the other terminal of the detection resistor;

level detector for detecting the level of a signal which develops between the terminals of the detection resistor and is an object of detection; and percent body fat computer for determining percent body fat on the basis of a result of detection operation performed by the level detector, wherein a measurement signal produced by the signal generator is made analogous to a half-wave waveform; and the level detector detects the level of a waveform analogous to a half-wave of the signal to be detected.

Specifically, the measurement signal is analogous to a half-wave waveform. Hence, when the level detector detects the level of a waveform analogous to a half-wave, the thus-detected level is substantially equal to the amplitude of a signal before rectification. Specifically, as in the case of use of a sinusoidal waveform, the level of a rectified signal is prevented from being reduced to one-half the amplitude of the signal before rectification.

In addition to the configuration set forth, the signal generator also has;

pulse generator for generating a pulse signal indicating the cycle of the measurement signal, a first resistor of which one terminal is connected to an output terminal of the pulse generator, a second resistor of which one terminal is connected to the other terminal of the first resistor, a first p-n-p transistor of which base is connected to the other terminal of the second resistor, of which collector is grounded, and of which emitter is connected to a positive power supply via a third resistor, a first capacitor of which one terminal is connected to a node between the first and second resistors and of which other terminal is connected to the emitter of the first p-n-p transistor, and a second capacitor connected between the base of the first p-n-p transistor and a ground level.

Specifically, a time constant determined by the first resistor and the first capacitor is set to a value close to one-half the cycle of the pulse signal. Further, a time constant determined by the second resistor and the second capacitor is made sufficiently smaller than the time constant determined by the first resistor and the first capacitor. In this case, a waveform analogous to a half-wave waveform appears on the emitter of the first p-n-p transistor during durations before and after a rising edge of a pulse signal. The signal generator for producing a half-wave waveform is formed from a small number of elements other than the pulse generator; that is, three resistors, two capacitors, and one p-n-p transistor.

In addition to the configuration set forth, the level detector also has;

a third capacitor of which one terminal is connected to the second electrode, a second p-n-p transistor of which base is connected to the other terminal of the third capacitor, of which collector is grounded via a fourth resistor, and of which emitter is connected to the positive power supply via a fifth resistor, a bias circuit for supplying a bias current to a base of the second p-n-p transistor, and a rectifier circuit for rectifying an output from a collector of the second p-n-p transistor.

Specifically, the bias circuit can be formed from two resistors. The rectifier circuit can be formed from one diode, one resistor, and one capacitor. Accordingly, the level detector can be formed from a small number of elements; that is, five resistors, two capacitors, one p-n-p transistor, and one diode.

In addition to the configuration set forth, the signal generator also has;

pulse generator for generating a pulse signal indicating the cycle of the measurement signal, a first resistor of which one terminal is connected to an output terminal of the pulse generator, a second resistor of which one terminal is connected to the other terminal of the first resistor, a first n-p-n transistor of which base is connected to the other terminal of the second resistor, of which collector is connected to a positive power supply, and of which emitter is grounded via a third resistor, a first capacitor of which one terminal is connected to a node between the first and second resistors and of which other terminal is connected to an emitter of the first n-p-n transistor, and a second capacitor connected between a base of the first n-p-n transistor and a ground level.

Specifically, a time constant determined by the first resistor and the first capacitor is set to a value close to one-half the cycle of the pulse signal. Further, a time constant determined by the second resistor and the second capacitor is made sufficiently smaller than the time constant determined by the first resistor and the first capacitor. In this case, a waveform analogous to a half-wave waveform appears on the emitter of the first n-p-n transistor during durations before and after a rising edge of a pulse signal. The signal generator for producing a half-wave waveform is formed from a small number of elements other than the pulse generator; that is, three resistors, two capacitors, and one n-p-n transistor.

In addition to the configuration set forth, the level detector has;

a third capacitor of which one terminal is connected to the second electrode, a second n-p-n transistor of which base is connected to the other terminal of the third capacitor, of which collector is connected to the positive power supply via a fourth resistor, and of which emitter is grounded via a fifth resistor, a bias circuit for supplying a bias current to the base of the second n-p-n transistor, and a rectifier circuit for rectifying an output from the collector of the second n-p-n transistor.

Specifically, the bias circuit can be formed from two resistors. The rectifier circuit can be formed from one diode, one resistor, and one capacitor. Accordingly, the level detector can be formed from a small number of elements; that is, five resistors, two capacitors, one n-p-n transistor, and one diode.

In addition to the configuration set forth, the pulse generator has;

original pulse generator which is formed from a microcomputer and produces an original pulse signal indicating the cycle of the measurement signal, sixth resistor of which one terminal is connected to the positive power supply, and a switching element of which one terminal is connected to the other terminal of the sixth resistor, of which other terminal is grounded, and whose connection is controlled by an original pulse signal, wherein a node between the sixth resistor and the switching element is taken as a terminal for outputting the pulse signal.

Even when variations arise in the voltage of operating power to be supplied to the microcomputer, the high-level voltage of a pulse signal to be output remains constant at all times.

Further, to solve the problem, the invention provides a percent body fat measuring apparatus having;

first and second electrodes with which a living body is brought into contact;

a detection resistor of which one terminal is connected to the second electrode;

signal generator which produces a measurement signal whose waveform is analogous to a half-wave waveform and applies a produced measurement signal between the first electrode and the other terminal of the detection resistor;

level detector which detects the level of a waveform analogous to a half-wave of a signal developing between the terminals of the detection resistor and outputs a result of detection as a detection signal; and percent body fat computer for determining percent body fat on the basis of a level value of the detection signal;

the level detector having;

a connection capacitor of which one terminal is connected to the second electrode, a p-n-p transistor of which base is connected to the other terminal of the connection capacitor, of which collector is grounded via a first resistor, and of which emitter is connected to a positive power supply via a second resistor, a bias circuit for supplying a bias current to a base of the p-n-p transistor, and a rectifier circuit which rectifies an output from a collector of the p-n-p transistor and outputs a rectified output as the detection signal, the percent body fat measuring apparatus further comprising:

corrector for subtracting a level value of the detection signal (called a test mode level value) which is obtained by additionally imparting, to the p-n-p transistor given a bias current by the bias circuit, an additional bias current for shifting the level value of the detection signal while generation of the measurement signal is suspended, from a level value of the detection signal (called a measurement mode level value) which is output from the rectifier circuit when a living body comes into contact with the first and second electrodes while a measurement signal is being produced; and wherein the percent body fat computer determines percent body fat on the basis of a result of correction performed by the corrector.

Specifically, under the assumption that a relationship between two types of temperatures t1, t2 is defined as (t1<t2), that the level value of the detection signal 651 obtained at the temperature t1 during the measurement mode is taken as A, and that the level value of the detection signal obtained at the temperature t1 during the test mode (hereinafter called a "test mode level value") is taken as B, at the temperature t2 the measurement mode level value assumes (A+a) and the test mode level value assumes (B+b) even when no change arises in the bio-impedance (a>0, b>0). Therefore, when a value C to be obtained by subtracting the test mode level value from the measurement mode level value is determined, the value C is expressed as (C=A−B) when the temperature is t1. When the temperature is t2, the value C is expressed as {C=(A+a)−(B+b)}. More specifically, the value C is expressed as {C=(A−B)+(a−b)}. This signifies that the influence of the temperature is eliminated from the subtracted value C by subtracting, from the measurement mode level value, the test mode level value obtained at the same temperature as that used in the measurement mode, so long as an increment "a" attributable to a temperature rise arising during the measurement mode is made equal to an increment "b" attributable to a temperature rise arising during the test mode.

The invention also provides a percent body fat measuring apparatus having;

first and second electrodes with which a living body is brought into contact;

a detection resistor of which one terminal is connected to the second electrode;

signal generator which produces a measurement signal of which waveform is analogous to a half-wave waveform and applies a produced measurement signal between the first electrode and the other terminal of the detection resistor;

level detector which detects the level of a waveform analogous to a half-wave of a signal developing between the terminals of the detection resistor and outputs a result of detection as a detection signal; and percent body fat computer for determining percent body fat on the basis of a level value of the detection signal;

the level detector having;

a connection capacitor of which one terminal is connected to the second electrode, a p-n-p transistor of which base is connected to the other terminal of the connection capacitor, of which collector is grounded via a first resistor, and of which emitter is connected to a positive power supply via a second resistor, a bias circuit for supplying a bias current to a base of the p-n-p transistor, and a rectifier circuit which rectifies an output from a collector of the p-n-p transistor and outputs a rectified output as the detection signal, the percent body fat measuring apparatus comprising:

corrector for correcting a level value of the detection signal which is output from the rectifier circuit when a living body comes into contact with the first and second electrodes while a measurement signal is being produced through use of a level value of the detection signal which is obtained by additionally imparting, to the p-n-p transistor given a bias current by the bias circuit, an additional bias current for shifting the level value of the detection signal while generation of the measurement signal is suspended; and wherein the percent body fat computer determines percent body fat on the basis of a result of correction performed by the corrector.

Specifically, under the assumption that a relationship between two types of temperatures t1, t2 is defined as (t1<t2), that the level value of the detection signal 651 obtained at the temperature t1 during the measurement mode (hereinafter called a "measurement mode level value") is taken as A, and that the level value of the detection signal 651 obtained at the temperature t1 during the test mode (hereinafter called a "test mode level value") is taken as B, at the temperature t2 the measurement mode level value assumes (A+a) and the test mode level value assumes (B+b) even when no change arises in the bio-impedance (a>0, b>0). The measurement mode level value and the test mode level value include shifts attributable to temperature changes. Therefore, if the measurement mode level value is corrected by use of the test mode level value, a value "a" included in the measurement mode level value can be changed to a minute value.

The invention also provides a percent body fat measuring apparatus having;

first and second electrodes with which a living body is brought into contact;

a detection resistor of which one terminal is connected to the second electrode;

signal generator which produces a measurement signal whose waveform is analogous to a half-wave waveform and applies a produced measurement signal between the first electrode and the other terminal of the detection resistor;

level detector which detects the level of a waveform analogous to a half-wave of a signal developing between the terminals of the detection resistor and outputs a result of detection as a detection signal; and percent body fat computer for determining percent body fat on the basis of a level value of the detection signal;

the level detector having;

a connection capacitor of which one terminal is connected to the second electrode, an n-p-n transistor of which base is connected to the other terminal of the connection capacitor, of which collector is connected to a positive power supply via a first resistor, and of which emitter is grounded via a second resistor, a bias circuit for supplying a bias current to a base of the n-p-n transistor, and a rectifier circuit which rectifies an output from a collector of the n-p-n transistor, the percent body fat measuring apparatus comprising:

corrector for subtracting a level value of the detection signal which is obtained by additionally imparting, to the n-p-n transistor given a bias current by the bias circuit, an additional bias current for shifting the level value of the detection signal while generation of the measurement signal is suspended, from a level value of the detection signal which is output from the rectifier circuit when a living body comes into contact with the first and second electrodes while a measurement signal is being produced; and wherein the percent body fat computer determines percent body fat on the basis of a result of correction performed by the corrector.

Specifically, under the assumption that a relationship between two types of temperatures t1, t2 is defined as (t1<t2), that the level value of the detection signal 651 obtained at the temperature t1 during the measurement mode is taken as A, and that the level value of the detection signal obtained at the temperature t1 during the test mode (hereinafter called a "test mode level value") is taken as B, at the temperature t2 the measurement mode level value assumes (A−a) and the test mode level value assumes (B−b) even when no change arises in the bio-impedance (a>0, b>0). Therefore, when a value C to be obtained by subtracting the test mode level value from the measurement mode level value is determined, the value C is expressed as (C=A−B) when the temperature is t1. When the temperature is t2, the value C is expressed as $\{C=(A-a)-(B-b)\}$. More specifically, the value C is expressed as $\{C=(A-B)-(a-b)\}$. This signifies that the influence of the temperature is eliminated from the subtracted value C by subtracting, from the measurement mode level value, the test mode level value obtained at the same temperature as that in the measurement mode, so long as an increment "a" attributable to a temperature rise arising during the measurement mode is made equal to an increment "b" attributable to a temperature rise arising during the test mode.

The invention also provides a percent body fat measuring apparatus having;

first and second electrodes with which a living body is brought into contact;

a detection resistor of which one terminal is connected to the second electrode;

signal generator which produces a measurement signal whose waveform is analogous to a half-wave waveform and applies a produced measurement signal between the first electrode and the other terminal of the detection resistor;

level detector which detects the level of a waveform analogous to a half-wave of a signal developing between the terminals of the detection resistor and outputs a result of detection as a detection signal; and percent body fat computer for determining percent body fat on the basis of a level value of the detection signal;

the level detector having;

a connection capacitor of which one terminal is connected to the second electrode, an n-p-n transistor of which base is connected to the other terminal of the connection capacitor, of which collector is connected to a positive power supply via a first resistor, and of which emitter is grounded via a second resistor, a bias circuit for supplying a bias current to a base of the n-p-n transistor, and a rectifier circuit which rectifies an output from a collector of the n-p-n transistor, the percent body fat measuring apparatus comprising:

corrector for correcting a level value of the detection signal which is output from the rectifier circuit when a living body comes into contact with the first and second electrodes while a measurement signal is being produced through use of a level value of the detection signal which is obtained by additionally imparting, to the n-p-n transistor given a bias current by the bias circuit, an additional bias current for shifting the level value of the detection signal while generation of the measurement signal is suspended; and wherein the percent body fat computer determines percent body fat on the basis of a result of correction performed by the corrector.

Specifically, under the assumption that a relationship between two types of temperatures t1, t2 is defined as (t1<t2), that the level value of the detection signal 651 obtained at the temperature t1 during the measurement mode is taken as A, and that the level value of the detection signal obtained at the temperature t1 during the test mode (hereinafter called a "test mode level value") is taken as B, at the temperature t2 the measurement mode level value assumes (A−a) and the test mode level value assumes (B−b) even when no change arises in the bio-impedance (a>0, b>0). The measurement mode level value and the test mode level value include shifts attributable to temperature changes. Therefore, if the measurement mode level value is corrected by use of the test mode level value, a value "a" included in the measurement mode level value can be changed to a minute value.

DETAILED DESCRIPTION OF THE PREFERRED EMBODIMENTS

An embodiment of the invention will be described hereinbelow by reference to the drawings.

(First Embodiment)

Figure 4:
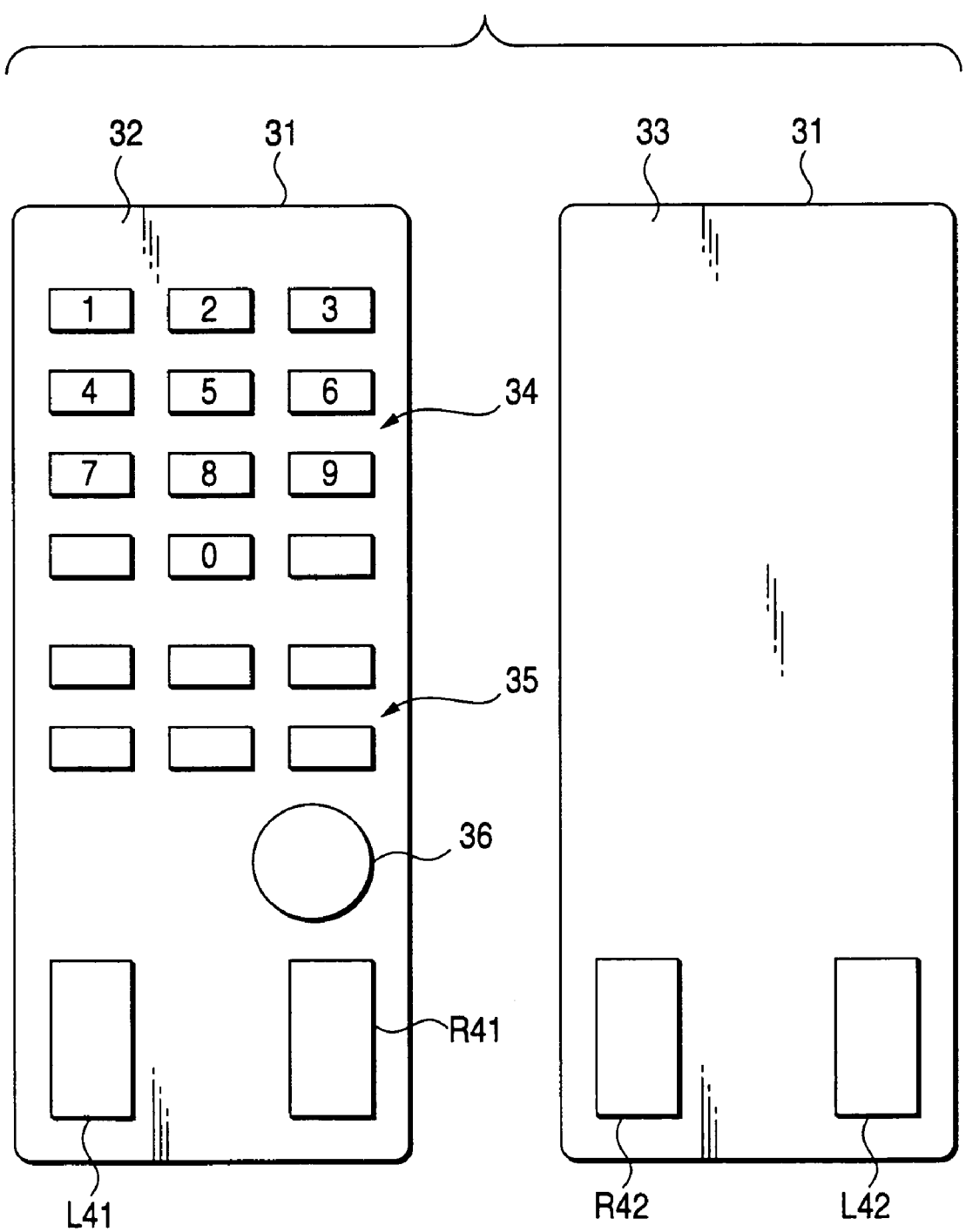
FIG. 4 is a descriptive view showing an external shape of the percent body fat measuring apparatus of the embodiment.

FIG. 4 is a descriptive view showing an outside shape of an embodiment of a percent body fat measuring apparatus according to the invention; specifically, a percent body fat measuring apparatus which has, in addition to the function of measuring percent body fat, the function of a remote control for a television set.

In relation to the drawing, numeric keys 34 to be used for entering a height and a weight or for instructing a channel are provided on an operation surface 32 of a main body 31. The operation surface 32 is also equipped with a plurality of mode keys 35 to be used for switching between operation of the percent body fat measuring apparatus and operation of the remote control. Moreover, the surface 32 is equipped with a measurement key 36 to be used for instructing initiation of measurement of percent body fat (other keys and switches are provided on an actual apparatus, but are omitted from the drawing).

Figure 5:
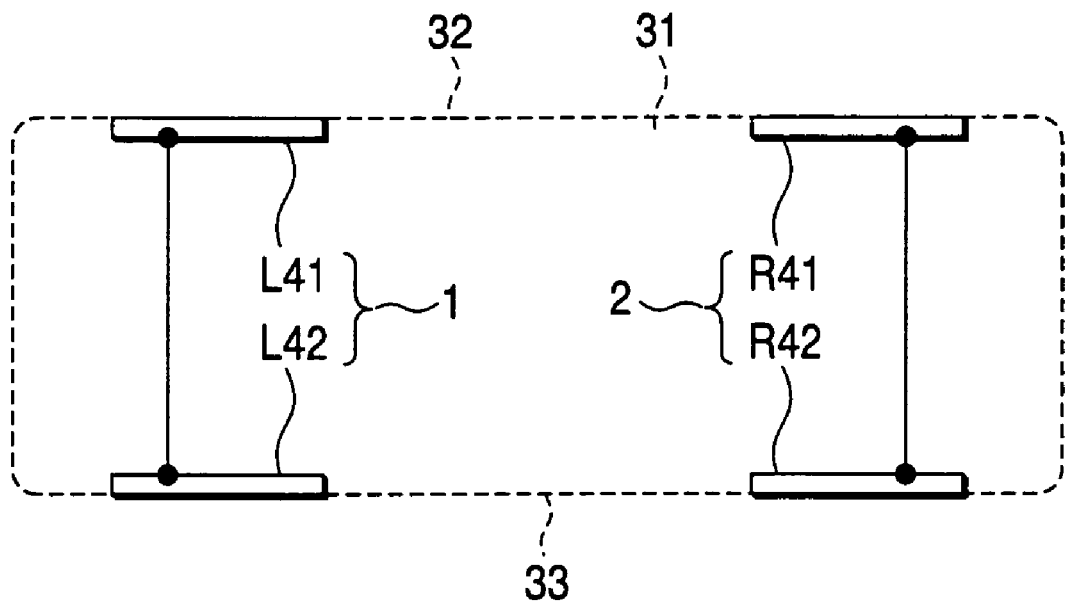
FIG. 5 is a descriptive view showing details of electrodes.

A pair of electrode plates L41, R41, with which the thumbs of a user are to be brought into contact at the time of measurement of percent body fat, are provided at lower right and left positions on the operation surface 32. Electrode plates L42, R42 are provided at positions on a back 33 of the main unit 31 corresponding to the electrodes L41, R41 provided on the operation surface 32. As shown in FIG. 5, the electrode plates L41, L42 are electrically connected together within the main unit 31, thereby constituting a first electrode. The electrode plates R41, R42 are also electrically connected together within the main unit 31, thereby constituting a second electrode.

More specifically, the first and second electrodes are formed from the electrode plates L41, R41 provided on the operation surface 32 and the electrode plates L42, R42 provided on the back 33. Accordingly, at the time of measurement of percent body fat, the left thumb and the left forefinger can be readily brought into contact with the first electrode with comparatively strong pressing force. The same also applies to the relationship between the right thumb, the right forefinger, and the second electrode. The first and second electrodes assume shapes which readily cause contact impedances—which arise at the first and second electrodes—to assume comparatively small values.

Figure 2:
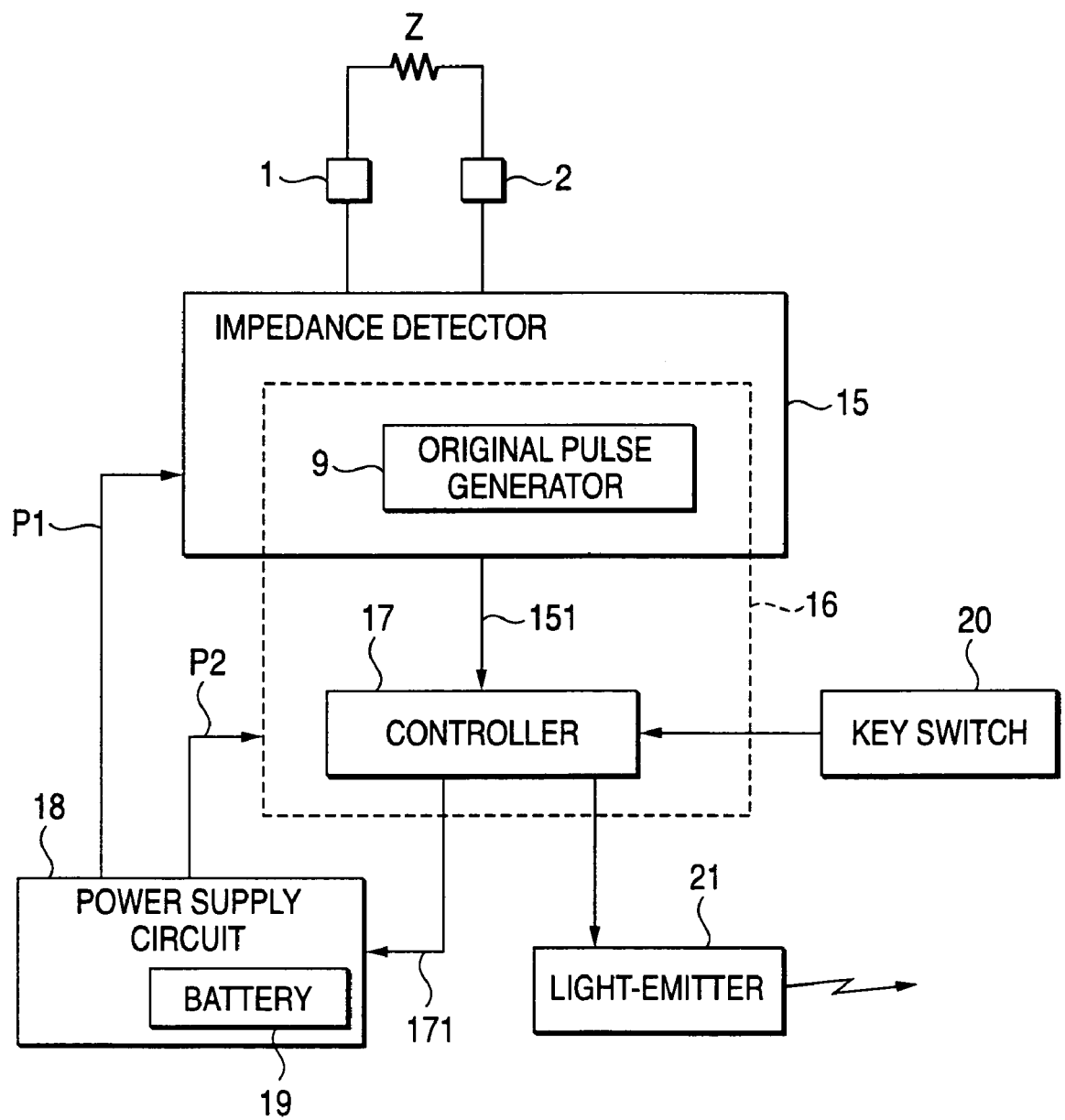
FIG. 2 is a block diagram showing an electrical configuration of the impedance detector of the embodiment.

FIG. 2 is a block diagram showing an electrical configuration of the embodiment.

Impedance detector 15 constitutes a block (which will be described in detail later) for sending, to controller 17, a detection output 151 whose voltage corresponds to impedance Z connected between the first electrode 1 and the second electrode 2. A key switch 20 constitutes a block formed from the numeric keys 34, the mode keys 35, and the measurement key 36, all being shown in FIG. 4, in conjunction with other, unillustrated keys.

Figure 9:
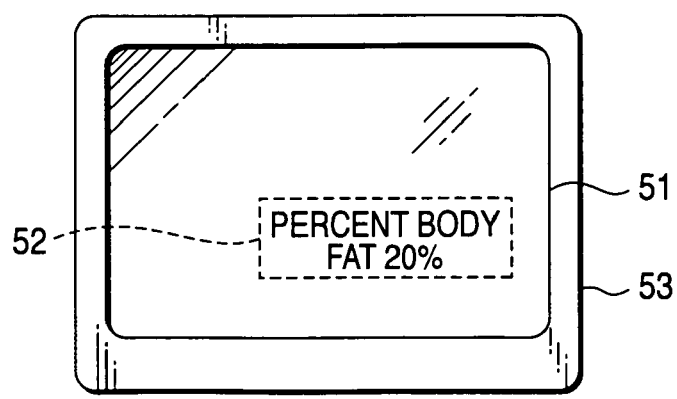
FIG. 9 is a descriptive view showing a screen on which percent body fat is to be displayed.

Transmitting device 21 constitutes a block formed from an infrared-emitting diode or the like for emitting an infrared ray to a television set 53 shown in FIG. 9. A power supply circuit 18 constitutes a block (to be described in detail later) which employs a battery 19 as a power source and generates a 4-volt stabilized positive power supply P1 for use in the impedance detector 15 and a positive power supply P2 for use in a microcomputer 16.

The controller 17 constitutes a block for controlling essential operations of a percent body fat measuring apparatus having the function of a remote controller. To this end, when the function of the remote controller is to be performed, the controller 17 performs control operation for transmitting an infrared signal corresponding to operation of the key switch 20. When operation of the percent body fat measuring apparatus is to be performed, the controller 17 enables entry of a height and a weight through use of the key switch 20. Further, the controller 17 constitutes percent body fat computer which computes percent body fat on the basis of the voltage of the detection output 151 from the impedance detector 15 and the entered height and weight. In order to display the thus-computed percent body fat in an area 52 on a screen 51 of the television set 53, an infrared signal indicating the percent body fat is transmitted from the light-emitter 21.

Original pulse generator 9 constituting one of the constituent elements of the impedance detector 15 is embodied as one of features of the microcomputer 16 constituting the controller 17.

Figure 3:
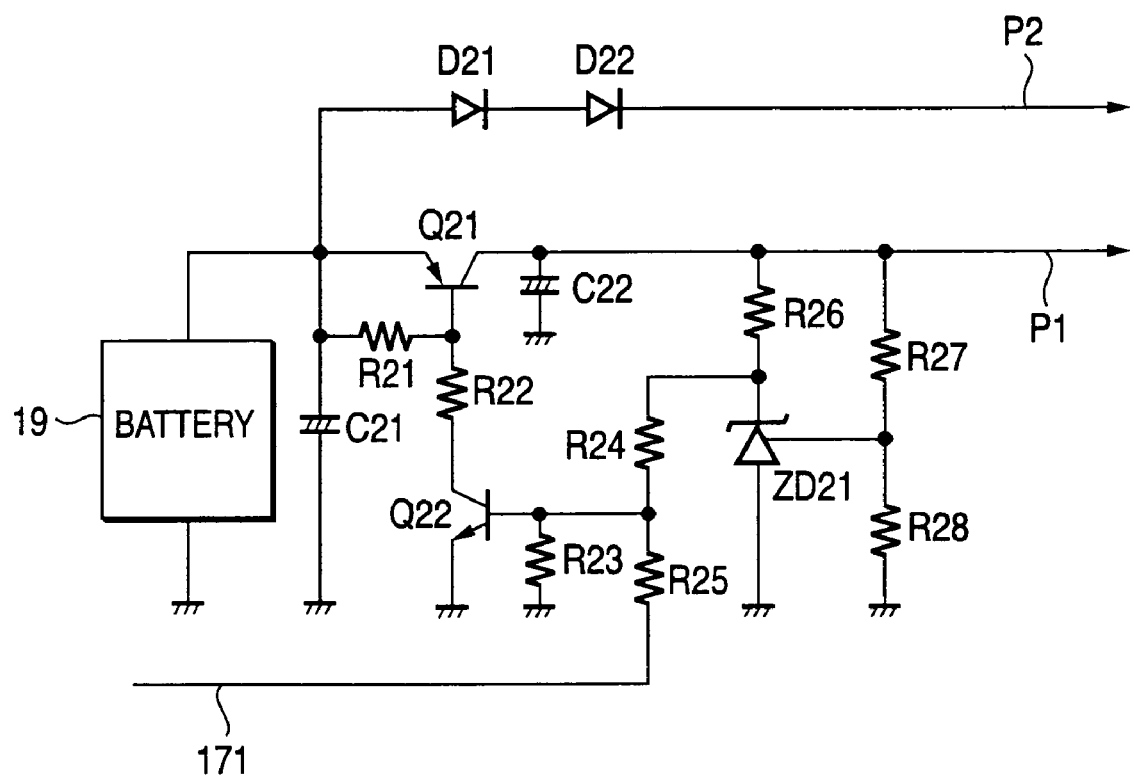
FIG. 3 is a circuit diagram showing a detailed electrical connection of a power supply circuit of the percent body fat measuring apparatus of the embodiment.

FIG. 3 is a circuit diagram showing a detailed electrical connection of the power supply circuit 18. The battery 19 serving as a power source is constituted of four manganese cells. Specifically, the battery 19 serves as a power source which produces a maximum voltage of about 7 volts and whose output voltage gradually decreases in association with a degree of usage. The power voltage of the microcomputer 16 ranges from 3 to 6 volts. Therefore, the positive power supply P2 supplied to the microcomputer 16 is supplied from the battery 19 via the two diodes D21, D22 connected in series. Specifically, the positive power supply P2 is a stable.

A capacitor C21 connected in parallel with the battery 19 serves as an element for equivalently reducing internal resistance of the battery 19. A resistor R21 connected between the emitter and base of a transistor Q21 serves as an element for increasing a base potential to an emitter potential. A capacitor C22 connected between the collector of the transistor Q21 and a ground level serves as an element for reducing output impedance. A shunt regulator ZD21 controls an electric current flowing through a resistor R26 such that a voltage divided by resistors R27 and R28 assumes a value of 2.5 volts. A transistor Q22 serves as an element for controlling the base current of the transistor Q21 in accordance with the cathode voltage of the shunt regulator ZD21; i.e., the electric current flowing through the resistor R26.

Here, a resistor R22 is an element for limiting a base current; a resistor R23 is an element for reducing base impedance of the transistor Q22; and a resistor R24 is an element for limiting a base current of the transistor Q22. A power control output line 171 originating from the controller 17 is introduced to the base of the transistor Q22 via a resistor R25.

The power supply circuit 18 has the foregoing configuration. Provided that a voltage is output from the collector of the transistor Q21, the shunt regulator ZD21 controls the electric current flowing through the resistor R26 such that a divided voltage assumes a value of 2.5 volts. Consequently, when the voltage of the positive power supply P1 attempts to increase, the base current of the transistor Q21 is controlled so as to decrease. When the voltage of the positive power supply P1 attempts to decrease, the base current of the transistor Q21 is controlled so as to increase. Therefore, the voltage of the positive power supply P1 is stabilized at a value of 4.0 volts.

In this way, when a low-level signal is sent through the power control output line 171 with the voltage of the positive power supply P1 being stabilized, the transistor Q22 is turned off. When the transistor Q22 is turned off, the transistor Q21 is also turned off. Consequently, the voltage of the positive power supply P1 assumes a value of zero volts.

When a high-level signal is sent through the power control output line 171 with the voltage of the positive power supply P1 assuming zero volts, a collector current flows into the transistor Q22, and an electric current also flows into the transistor Q21. As a result, the voltage of the positive power supply P1 is stabilized at a value of four volts. This state is also maintained even when the power control output 171 has high impedance. Consequently, after the high-level signal is sent through the power control output 171 within a short period of time; e.g., 50 mS, with the positive power supply P1 assuming a value of zero volts, the positive power supply P1 is stabilized at four volts even when the power control output 171 is brought into high impedance.

When the voltage of the positive power supply P1 and that of the positive power supply P2 are compared with each other, the voltage of the positive power supply P2 varies according to variations in the voltage of the battery 19. Accordingly, under the assumption that forward voltages of the respective diodes D21, D22 assume a value of 0.6 volts, when the voltage of the battery 19 is higher than 5.2 volts, the voltage of the positive power supply P2 is higher than the voltage of the positive power supply P1. In contrast, when the voltage of the battery 19 is lower than 5.2 volts, the voltage of the positive power supply P2 is lower than that of the positive power supply P1. Namely, a relative relationship between the voltage of the positive power supply P1 and the voltage of the positive power supply P2 is changed.

The detailed descriptions of the power supply circuit 18 are now completed. By reference to FIG. 1, a detailed configuration of the impedance detector 15 will be described hereinbelow. The impedance detector 15 broadly comprises signal generator 3; level detector 4; two diodes D4, D5; and two resistors R13, R14.

Specifically, the resistor R14 acts as a detection resistor which will be described in claims, and one terminal of the resistor R14 is connected to a second electrode 2 and the other terminal of the same is grounded. The signal generator 3 produces a signal to be used for measuring a waveform analogous to a half-wave waveform (the signal will be hereinafter called a "measurement signal"). The thus-generated measurement signal is applied between the first electrode 1 and the other terminal (at a ground level) of the detection resistor R14. The level detector 4 constitutes a block for detecting the level of a waveform analogous to a half-wave of a signal which is an object of detection and develops between the terminals of the detection resistor R14.

More specifically, the signal generator 3 has pulse generator 5 for producing a pulse signal indicating the cycle of the measurement signal, and a half-wave signal generation circuit 6 for generating a measurement signal whose waveform is analogous to a half-wave waveform.

Further specifically, the pulse generator 5 is a block formed from some of the functions of the microcomputer 16 and has original pulse generator 9 for producing an original pulse signal of 50 KHz which indicates the cycle of the measurement signal. The pulse generator 5 also has a resistor R7 of which one terminal is connected to an output terminal of the original pulse generator 9; and an n-p-n transistor (switching element) Q3 of which base is connected to the other terminal of the resistor R7, of which emitter is grounded, and of which collector is connected to the positive power supply P1 via a sixth resistor R6. The collector of the n-p-n transistor Q3 serves as an output terminal of the pulse generator 5, from which a pulse signal is sent to the half-wave signal generation circuit 6. A series circuit comprising a capacitor C11 and a resistor R11 acts as a speedup circuit for speeding up the switching speed of the n-p-n transistor Q3.

As can be seen from the above descriptions, the n-p-n transistor Q3 performs switching operation such that the transistor is turned on when the original pulse signal becomes high and is turned off when the original pulse signal becomes low. Accordingly, even when the high-level voltage of the original pulse signal varies in accordance with variations in the voltage of the battery 19 (the high-level voltage is equal to the voltage of the positive power supply P2), the pulse generator 5 transmits, to the half-wave signal generation circuit 6, a pulse signal whose high-level voltage is equal to the voltage of the positive power supply P1.

Specifically, the half-wave signal generation circuit 6 has a first resistor R1 of which one terminal is connected to the collector of the n-p-n transistor Q3 (i.e., the output terminal of the pulse generator 5), and a second resistor R2 of which one terminal is connected to the other terminal of the first resistor R1. The half-wave signal generation circuit 6 also has a first p-n-p transistor Q1 of which base is connected to the other terminal of the second resistor R2, of which collector is grounded, and of which emitter is connected to the positive power supply P1 via a third resistor R3.

In addition, the half-wave signal generation circuit 6 has a first capacitor C1 of which one terminal is connected to a node between the first and second resistors R1, R2 and of which other terminal is connected to the emitter of the first p-n-p transistor Q1, and a second capacitor C2 connected between the base of the first p-n-p transistor Q1 and the ground level. The first resistor R1 is connected in shunt with a diode D1 such that an electric current flows from the pulse generator 5 to the second resistor R2. The emitter of the first p-n-p transistor Q1 is connected to the first electrode 1 via a resistor R12. Diodes D2, D3 are elements for protecting the half-wave signal generation circuit 6 when static electricity is applied to the first electrode 1.

The level detector 4 will now be described in detail. The level detector 4 has a third capacitor C3 of which one terminal is connected to the second electrode 2 via a resistor R15. Here, the resistor R15 acts as an element for increasing impedance of the level detector 4 with respect to the second electrode 2. The level detector 4 also has a second p-n-p transistor Q2 of which base is connected to the other terminal of the third capacitor C3, of which collector is grounded via a fourth resistor R4 which is to serve as load impedance, and of which emitter is connected to the positive power supply P1 via a fifth resistor R5 which affords a negative feedback. Further, the level detector 4 has a bias circuit 7 which comprises resistors R16, R17 and which supplies a bias current to the base of the second p-n-p transistor Q2.

In addition, the level detector 4 has a rectifier circuit 8 which rectifies an output from the collector of the second p-n-p transistor Q2. The rectifier circuit 8 has a diode D6 of which anode is connected to the collector of the second p-n-p transistor Q2 and of which cathode serves as an output terminal of the rectifier circuit 8. The rectifier circuit 8 also has a capacitor C12 connected between the cathode of the diode D6 and the ground level and a resistor R18 connected in shunt with the capacitor C12.

The diodes D4, D5 act as elements for protecting the level detector 4 when static electricity is applied to the second electrode 2. A resistor R13 connected between the second electrode 2 and the positive power supply P1 acts as an element for shifting a voltage developing between terminals of a detection resistor R14 toward a positive range.

Figure 7:
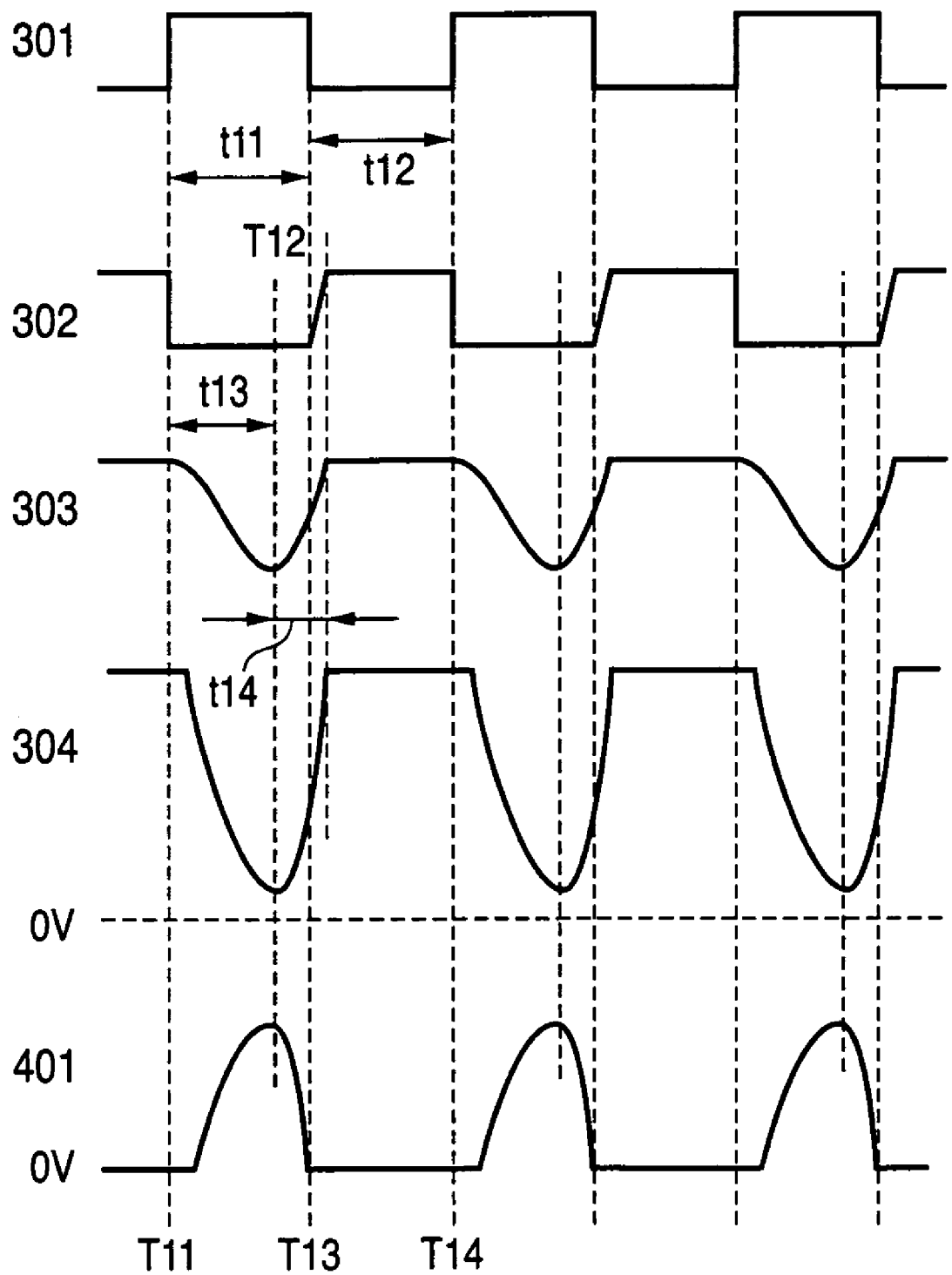
FIG. 7 is a descriptive view showing waveforms of primary signals appearing when p-n-p transistors are used as elements.

FIG. 7 is a descriptive view showing signal waveforms appearing at primary points in the signal generator 3. Operation of the signal generator 3 will be described by reference to FIG. 7 when necessary.

An original pulse signal 301 is a 50-kHz signal. Therefore, a high-level duration t11 of the original pulse signal 301 and a low-level duration t12 of the same assume a value of 10 μS. Hence, if a slope appearing at the rising edge of a pulse signal 302 output from the pulse generator 5 to the half-wave generation circuit 6 is ignored, a high-level duration of the pulse signal and a low-level duration of the same also assume a value of 10 μS.

In relation to values of the elements, the first resistor R1 assumes a value of 10 kΩ; the first capacitor C1 assumes a value of 0.0015 μF; the second resistor R2 assumes a value of 2.7 kΩ; and the second capacitor C2 assumes a value of 100 pF. The resistor R6 to be used for increasing the pulse signal 302 to a high level assumes a value of 2.7 kΩ. Therefore, a time constant determined by the first resistor R1 and the first capacitor C1 assumes a value of 15 μS. A time constant determined by the second resistor R2 and the second capacitor C2 assumes a value sufficiently shorter than 15 μS. When an electric current flows toward the ground via the first resistor R1 and the third n-p-n transistor Q3, the diode D1 can be ignored.

As mentioned above, when a duration t13 of about 7.5 μS has lapsed from time T11 at which the pulse signal 302 falls (i.e., at time T12), the emitter potential of the first p-n-p transistor Q1 reaches the minimum value. Subsequently, when another duration of about 7.5 μS has lapsed, the emitter potential of the first p-n-p transistor Q1 increases to a potential equal to that obtained at time T11.

However, when the pulse signal 302 rises at time T13, an electric current flows into the diode D1. Consequently, at time T13 or at any subsequent point in time, the base potential of the first p-n-p transistor Q1 increases in accordance with a time constant of 2.7 μS determined by the resistor R6 and the first capacitor C1. As a result, the emitter potential of the first p-n-p transistor Q1 increases, within a period t14 shorter than t13, to a voltage equal to that obtained at time T11. When time T14 has come, operation identical with that performed from time T11 is resumed.

In consequence of the foregoing operation, a measurement signal 304 appearing at the emitter of the first p-n-p transistor Q1 assumes a waveform similar to a half-wave waveform. Further, the amplitude of the half-wave approximates the voltage of the positive power supply P1 (i.e., four volts) (in a real apparatus the voltage is about 3.5 volts).

As is obvious from the foregoing description, when the capacitance of the first capacitor C4 is set to 0.001 μF or the like and when a time constant defined between the first resistor R1 and the first capacitor C1 is set to about 10 μS, the diode D1 can be omitted from the configuration.

Explanations of operation of the half-wave signal generation circuit 6 are now completed, and operation of the level detector 4 will now be described.

A half-wave waveform whose amplitude corresponds to a value of the bio-impedance Z connected between the first and second electrodes 1, 2 appears at the second electrode 2 connected to the detection resistor R14. The half-wave waveform appearing at the second electrode 2 is amplified by the second p-n-p transistor Q2, and the thus-amplified waveform is output from the collector (indicated by 401 in FIG. 7). Further, provided that the value of the fourth resistor R4 is set so as to become sufficiently larger than the value of the fifth resistor R5 (about 30 times in the real apparatus), the maximum amplitude of the half-wave waveform 401 output from the collector can be made to approximate the voltage of the positive power supply P1.

In light of the foregoing description, when the bio-impedance Z connected between the first and second electrodes 1, 2 assumes the minimum value within the range of measurement, the amplitude of the half-wave waveform output from the collector of the second p-n-p transistor Q2 can be made to approximate the positive power supply P1 by means of setting an amplification factor of the second p-n-p transistor Q2 to an appropriate value. In this case, the level of the detection output 151 from the rectifier circuit 8 assumes a value of 3.4 volts obtained by subtracting the forward voltage of the diode D6 from the voltage of the positive power supply P1; that is, a value of four volts. Specifically, the detection output 151 varies within the range from 0 to 3.4 volts. In other words, the detection output 151 has a sufficiently-wide dynamic range.

Figure 8:
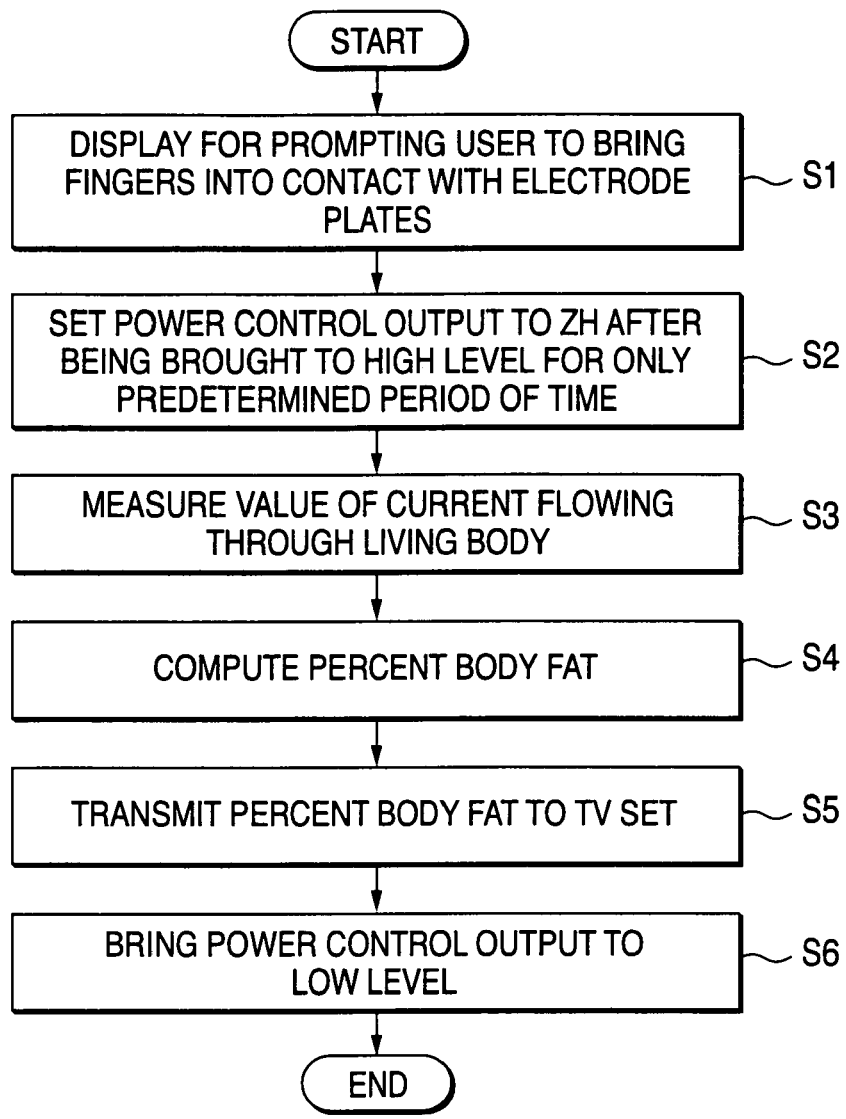
FIG. 8 is a flowchart showing the primary operation of the percent body fat measuring apparatus to be performed at the time of measurement of percent body fat.

The detailed explanation of the impedance detector 15 is now completed. Operation of the percent body fat measuring apparatus to be performed at the time of measurement of percent body fat will now be described by reference to a flowchart provided in FIG. 8.

When percent body fat is not measured, the controller 17 brings the power control output line 171 to a low level, thereby bringing the positive power supply P1 to zero volts and preventing unwanted consumption of the battery 19. It is also assumed that the weight and height of a user who attempts to measure percent body fat are already input. It is assumed that, in this state, the user supports the main unit 31 such that an infrared ray is transmitted to the television set 53 and operates the measurement key 36, the controller 17 displays, on the screen 51 of the television set 53, a message for prompting the user to bring his or her left thumb into contact with the electrode plate L41, the left forefinger into contact with the electrode plate L42, the right thumb into contact with the electrode plate R41, and the right forefinger into contact with the electrode plate R42 (step S1).

Figure 6:
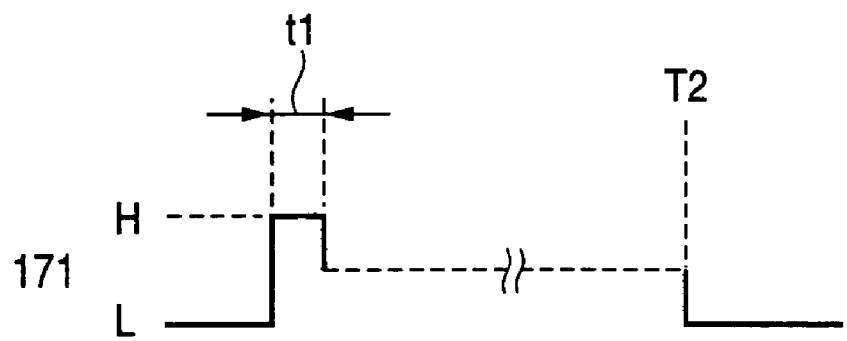
FIG. 6 is a descriptive view showing the waveform of a signal to be used for controlling the power supply circuit.

As shown in FIG. 6, the voltage of the positive power supply P1 is increased from zero to four volts by rendering the impedance of the power control output 171 high after the power control output 171 is brought to a high level for only the duration t1 (e.g., 50 mS). The impedance detector 15 is set to the operating state (step S2). Subsequently, the voltage of the detection output 151 is measured through use of an internal analog-to-digital converter (step S3). Next, percent body fat is computed from a result of measurement and the previously-input weight and height (step S4). The thus-computed percent body fat is displayed on the screen 51 of the television set 53 (step S5). Subsequently, the power control output 171 is brought to a low level (time T2 in FIG. 6), and the voltage of the positive power supply P1 is set to zero volts, thereby deactivating the impedance detector 15 (step S6). Consequently, the thus-measured percent body fat is displayed in the area 52 of the screen 51 of the television set 53.

Figure 1:
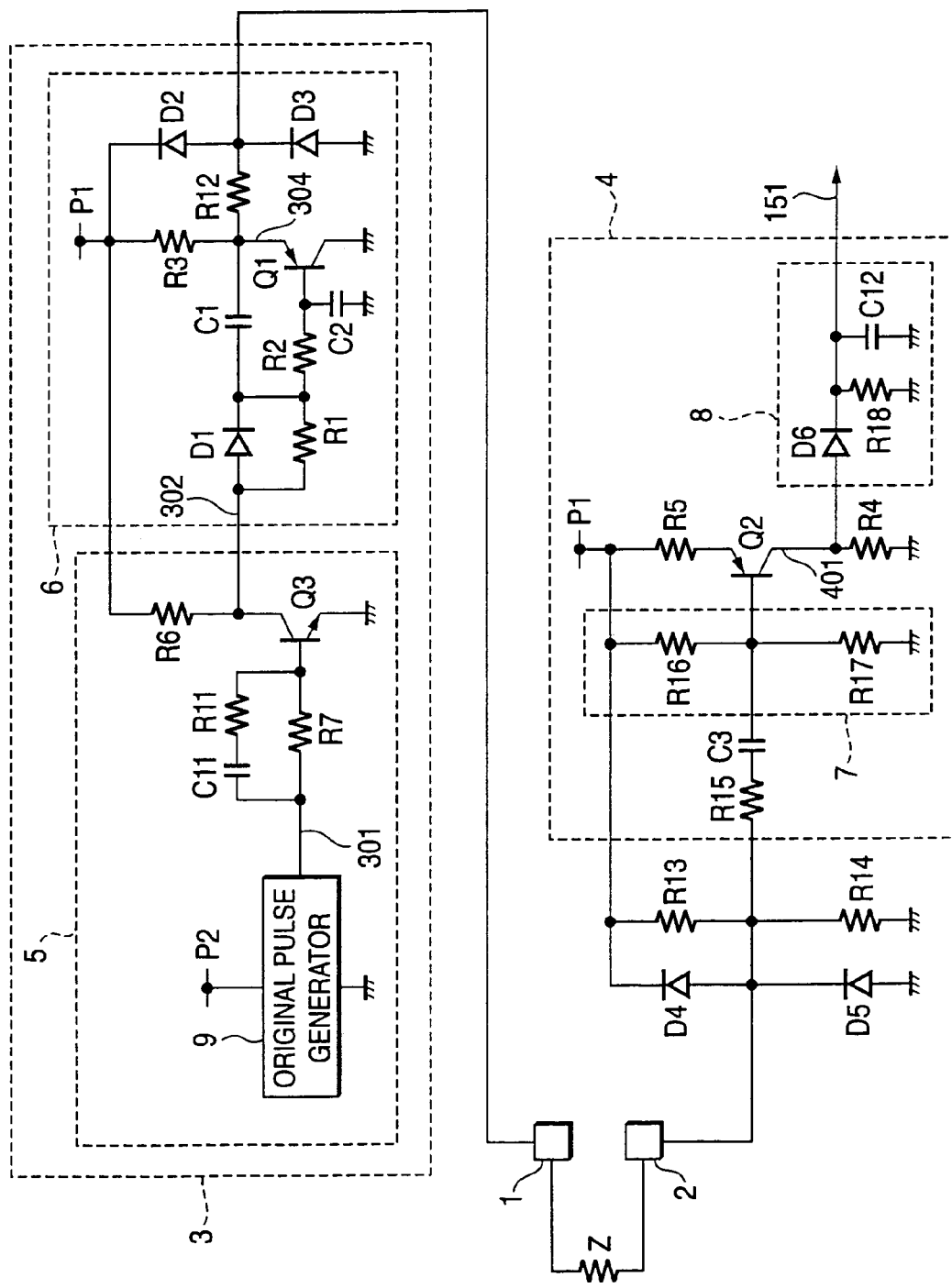
FIG. 1 is a circuit diagram showing a detailed electrical connection of impedance detector of a percent body fat measuring apparatus according to an embodiment of the invention.
Figure 10:
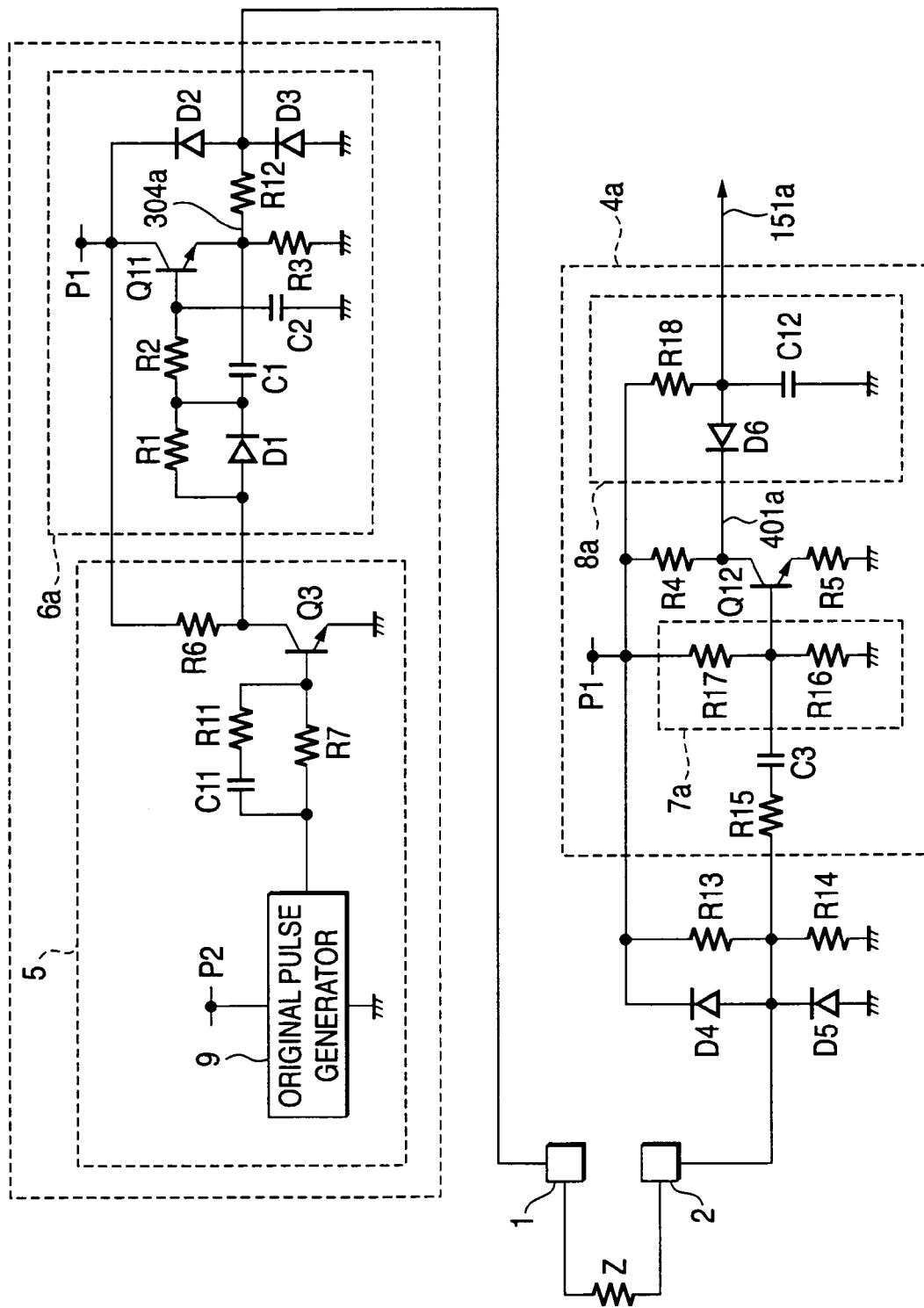
FIG. 10 is a circuit diagram showing a detailed electrical connection of impedance detector required when n-p-n transistors are used as elements.

By reference to FIG. 10, the configuration of the percent body fat measuring apparatus will be described when the first p-n-p transistor Q1 of the half-wave signal generation circuit 6 and the second p-n-p transistor Q2 of the level detector 4 are changed to n-p-n transistors. Throughout the drawings, elements which are identical in operation and configuration with those shown in FIG. 1 are assigned the same reference numerals as used in FIG. 1. Therefore, an explanation is now given of only a configuration difference between the percent body fat measuring apparatus shown in FIG. 10 and that shown in FIG. 1.

The first p-n-p transistor Q1 shown in FIG. 1 is changed to a first n-p-n transistor Q11. The collector of the first n-p-n transistor Q11 is connected to the positive power supply P1 in accordance with such a change. Further, the third resistor R3 is connected between the emitter of the first n-p-n transistor Q11 and the ground level.

The second p-n-p transistor Q2 shown in FIG. 1 is changed to a second n-p-n transistor Q12. The fourth resistor R4 is connected between the collector of the second n-p-n transistor Q12 and the positive power supply P1 in accordance with the change. The fifth resistor R5 is connected between the emitter of the second n-p-n transistor Q12 and the ground level. Further, the resistors R16, R17 in the bias circuit 7a have changed their locations. The orientation of the diode D6 in a rectifier circuit 8a is changed, and the resistor R18 is connected between the anode of the diode D6 and the positive power supply P1.

Figure 11:
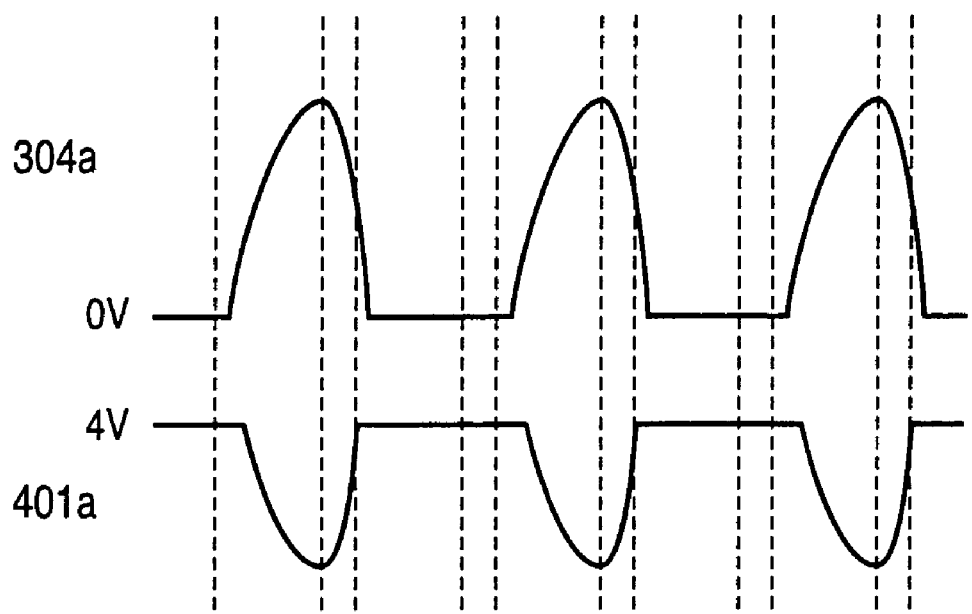
FIG. 11 is a descriptive view showing waveforms of primary signals appearing when n-p-n transistors are used as elements.

As indicated by reference numeral 304a in FIG. 11, the waveform of the measurement signal output from the half-wave signal generation circuit 6a having the foregoing configuration assumes a shape in which a half-wave waveform is formed in the direction in which the voltage increases. As indicated by reference numeral 401a in FIG. 11, the waveform of a collector signal of the second n-p-n transistor Q12 of the level detector 4a assumes a shape in which a half-wave waveform is formed in a position close to zero volts with four volts of the positive power supply P1 being taken as a reference potential. Accordingly, a detection output 151a sent from the rectifier circuit 8a changes so as to approach zero volts as the value of the bio-impedance Z becomes smaller.

Figure 12:
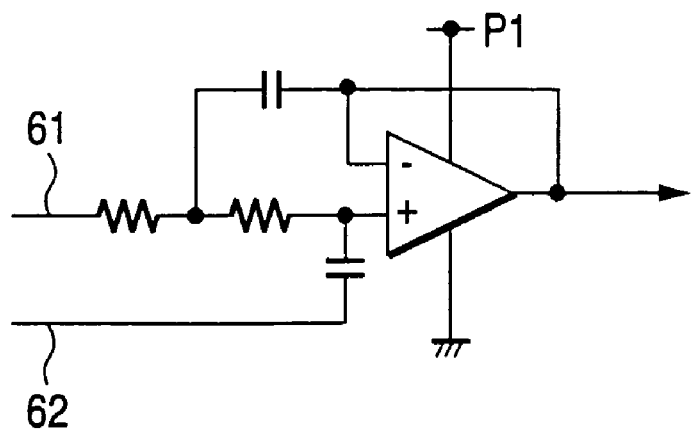
FIG. 12 is a circuit diagram showing an example configuration required when a measurement signal analogous to a half-wave waveform is generated through use of an operational amplifier.
Figure 13:
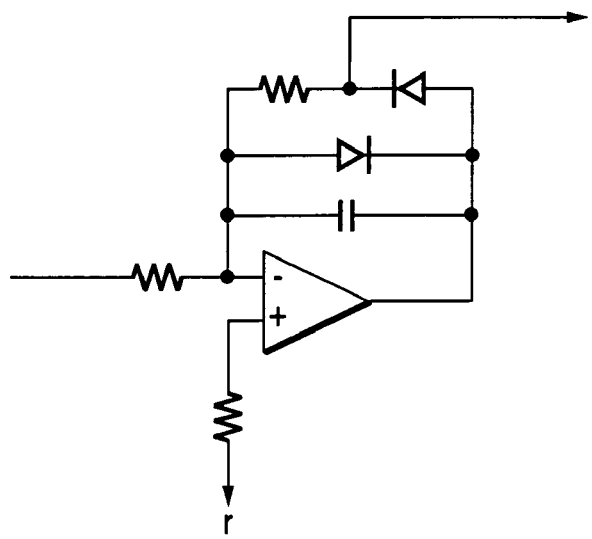
FIG. 13 is a circuit diagram showing a related-art technique employed in a rectifier circuit.
Figure 14:
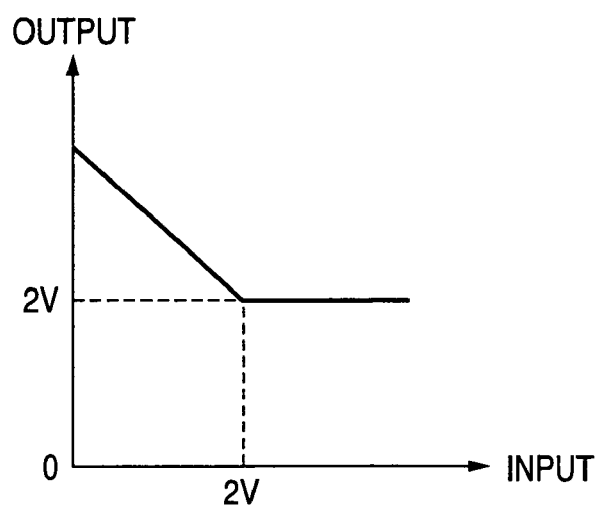
FIG. 14 is a descriptive view showing a relationship between an input level and an output level, both belonging to the rectifier circuit shown in FIG. 13.
Figure 15:
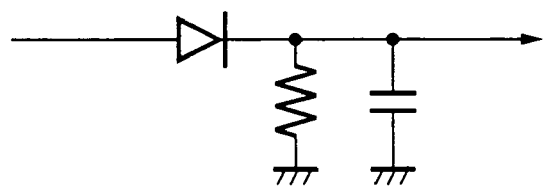
FIG. 15 is a circuit diagram showing a related-art technique of a rectifier circuit using a diode.

The half-wave signal generation circuit which produces a measurement signal analogous to a half-wave waveform on the basis of the pulse signal 302 can be constructed through use of an operational amplifier. FIG. 12 shows an example circuit configuration desirable in such a situation. The pulse signal 302 is led to a line 61, and a reference voltage is led to a line 62.

Now, an explanation is given of the reference voltage led to the line 62. When the level detector is constructed so as to assume the configuration shown in FIG. 1, the reference voltage 62 is made close to the voltage (e.g., 3.5 volts) of the positive power supply P1 in order to cause the operation amplifier 61 to output a measurement signal (a signal whose waveform is analogous to that indicated by 304) whose half-wave waveform is formed in a range close to zero volts. When the level detector is constructed so as to assume the configuration shown in FIG. 10, the reference voltage 62 is set to a voltage close to zero volts (e.g., 0.5 volts) in order to cause the operational amplifier 61 to output a measurement signal (i.e., a signal whose waveform is analogous to that indicated by 304a) in which a half-wave waveform is formed toward the voltage of the positive power supply P1.

In relation to a method of displaying percent body fat, an explanation is given of a case where the percent body fat measuring apparatus is configured so as to display percent body fat on the television set 53, which is an object of remote control. However, the remote control function of the apparatus can be omitted, and a display, such as an LCD, can be added to the percent body fat measuring apparatus, wherein percent body fat is displayed on the thus-added display.

(Second Embodiment)

Figure 17:
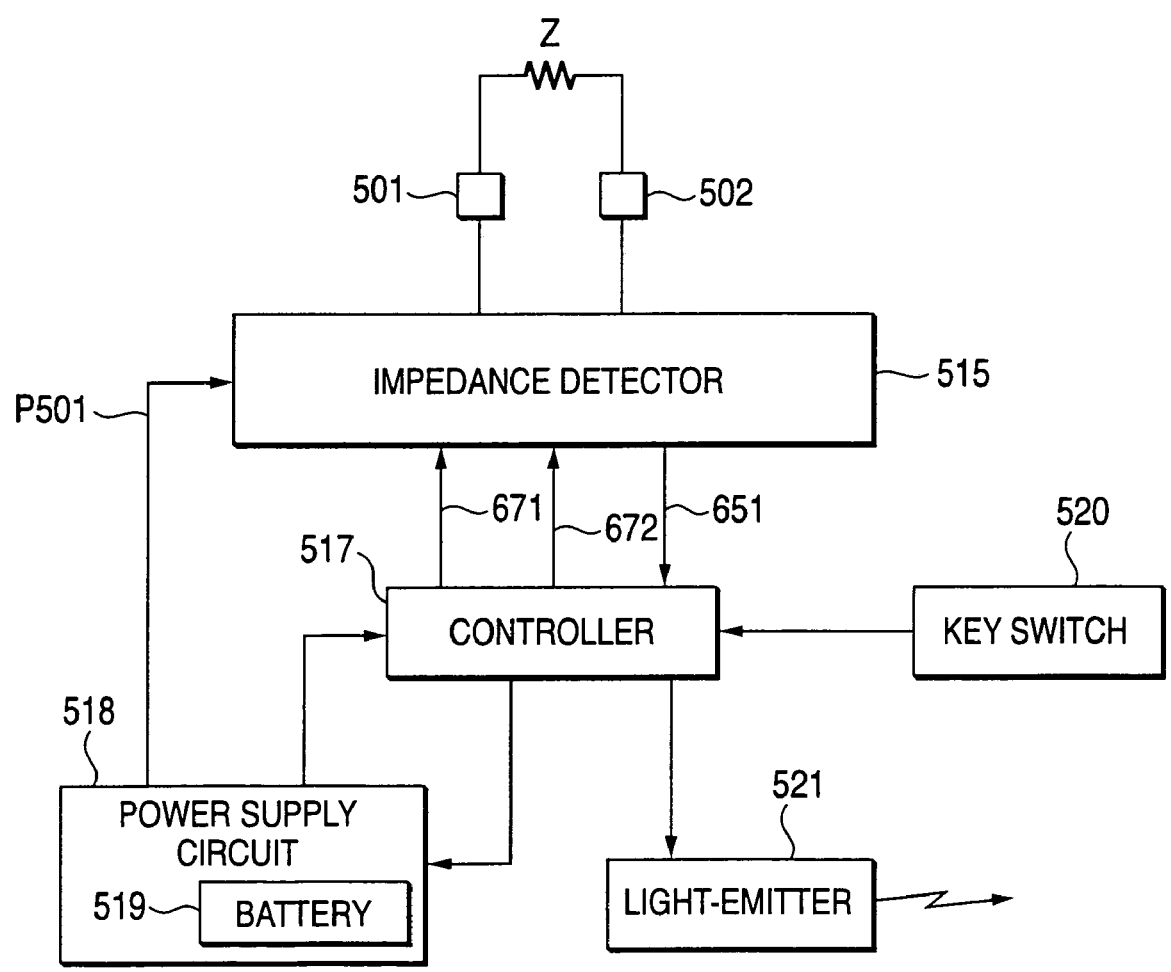
FIG. 17 is a block diagram showing an electrical configuration of the impedance detector of the embodiment.

Further, FIG. 17 is a block diagram showing an electrical configuration of the embodiment.

Impedance detector 515 constitutes a block (which will be described in detail later) for sending, to controller 517, a detection signal 651 which assumes a level corresponding to impedance Z connected between the first electrode 501 and the second electrode 502. A key switch 520 constitutes a block formed from the numeric keys 534, the mode keys 535, and the measurement key 536, in conjunction with other, unillustrated keys.

Figure 21:
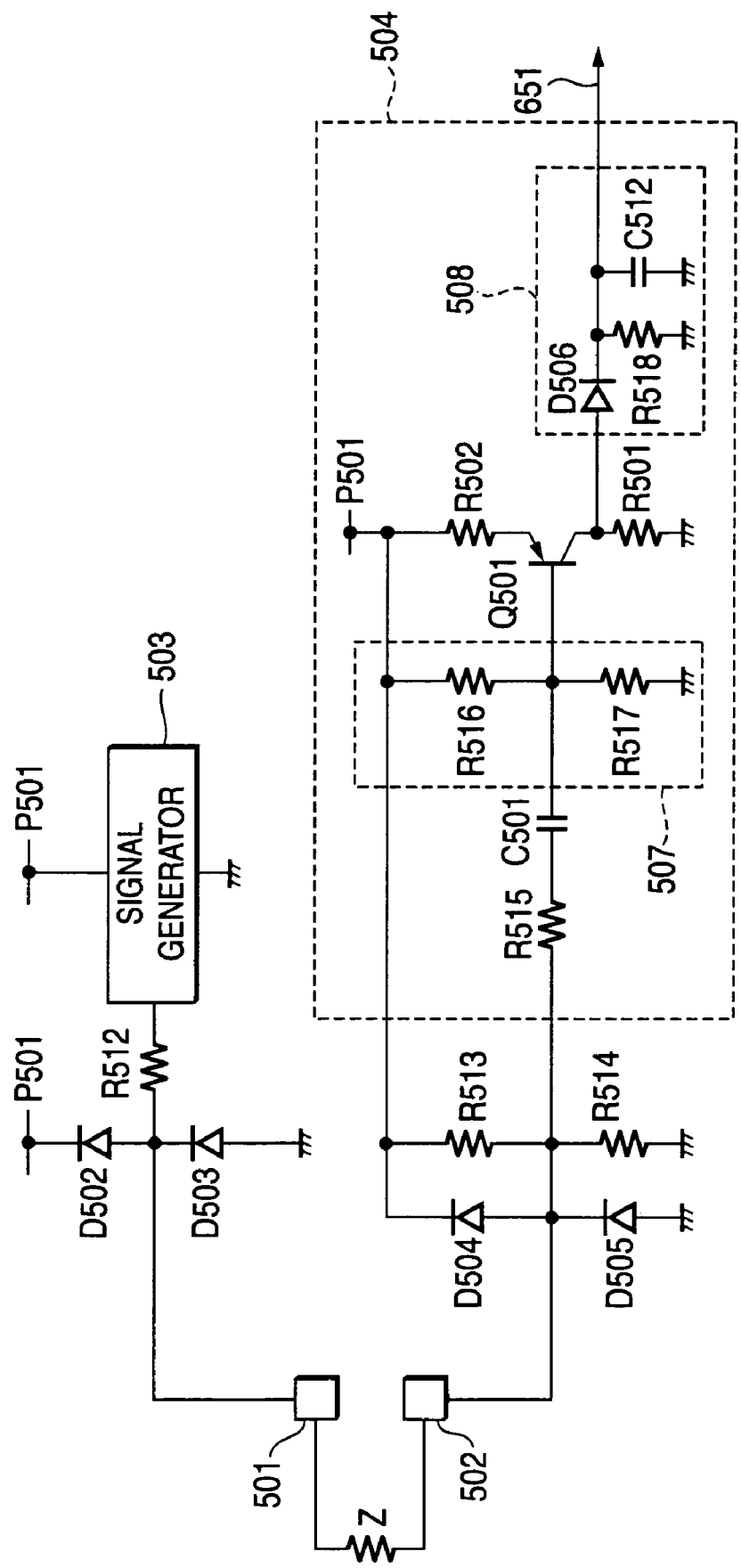
FIG. 21 is a circuit diagram showing an electrical connection of related-art level detector.

Before description of configuration of the controller 517, detailed configuration of the impedance detector 515 will be described by reference to FIG. 16. Those elements which are the same as those employed in the related art are assigned the same reference numerals as those provided in FIG. 21.

The impedance detector 515 broadly comprises signal generator 503; level detector 504; four diodes D502 to D505; and three resistors R512 to R514.

Specifically, the resistor R514 acts as a detection resistor which will be described in claims, and one terminal of the resistor R514 is connected to a second electrode 502 and the other terminal of the same is grounded. The signal generator 503 constitutes a block which produces a signal to be used for measuring a waveform analogous to a half-wave waveform (the signal will be hereinafter called a "measurement signal") while a pulse signal 671 of 50 KHz produced by the controller 517 is taken as an original signal. The thus-generated measurement signal is applied between the first electrode 501 and the other terminal (at a ground level) of the detection resistor R514. The level detector 504 constitutes a block for detecting the level of a waveform analogous to a half-wave of a signal developing between the terminals of the detection resistor R514. A result of detection is transmitted as the detection signal 651 to the controller 517.

The level detector 504 will now be described in detail. The level detector 504 has a connection capacitor C501 of which one terminal is connected to the second electrode 502 via a resistor R515. Here, the resistor R515 acts as an element for increasing impedance of the level detector 504 with respect to the second electrode 502. The level detector 504 also has a p-n-p transistor Q501 of which base is connected to the other terminal of the connection capacitor C501, of which collector is grounded via a first resistor R501 which is to serve as load impedance, and of which emitter is connected to a positive power supply P501 via a second resistor R502 which affords a negative feedback. Further, the level detector 504 has a bias circuit 507 which comprises resistors R516, R517 and which supplies a bias current to the base of the p-n-p transistor Q501.

In addition, the level detector 504 has a rectifier circuit 508 which rectifies an output from the collector of the p-n-p transistor Q501 and outputs the thus-rectified output as the detection signal 651. The rectifier circuit 508 has a diode D506 of which anode is connected to the collector of the p-n-p transistor Q501; a capacitor C512 connected between the cathode of the diode D506 and the ground level; and a resistor R518 connected in shunt with the capacitor C512.

The diodes D502, D503 and the resistor R512 are elements for protecting the signal generator 503 when static electricity is applied to the first electrode 501. Further, the diodes D504, D505 act as elements for protecting the level detector 504 when static electricity is applied to the second electrode 502. A resistor R513 connected between the second electrode 502 and the positive power supply P501 acts as an element for shifting a voltage developing between terminals of a detection resistor R514 toward a positive range.

A transistor Q502 of which collector is connected to the base of the p-n-p transistor Q501 via the resistor R506, of which emitter is grounded, and of which base is introduced to a control output 672 of the controller 517 via the resistor R504 serves as an element for additionally imparting, to the p-n-p transistor Q501 given a bias current from the bias circuit 507, a bias current which increases an output level of the rectifier circuit 508. When the control output 672 drops to a low level, the resistor R505 suppresses arise in base impedance of the transistor Q502.

Description of the detailed configuration of the impedance detector 515 is now completed, and the configuration of the controller 517 will now be described by turning back to FIG. 17.

The controller 517 acts as a block which is constituted of a microcomputer having an analog-to-digital converter for acquiring a value of level of the detection signal 651 output from the impedance detector 515 (hereinafter called a "level value of the detection signal 651"). The controller 517 controls essential operations of a percent body fat measuring apparatus having a remote control function. To this end, when operation of the remote control is to be performed, the controller 517 brings the positive power supply P501 to be fed to the impedance detector 515 to zero volts, by means of controlling the power supply circuit 518. Further, the controller 517 performs control operation for causing light-emitter 521 to transmit an infrared signal corresponding to operation of the key switch 520.

When operation of the percent body fat measuring apparatus is to be performed, the controller 517 enables entry of a height and a weight through use of the key switch 520 and stores the thus-entered height and weight. Further, the controller 517 brings the positive power supply P501 to four volts and the impedance detector 515 into an operating state, by means of controlling the power supply circuit 518.

A value of output level of the rectifier circuit 508 (i.e., the level value of the detection signal 651)—which would be achieved by additionally imparting, to the p-n-p transistor Q501, a bias current for shifting the output level of the rectifier circuit 508 with generation of the measurement signal being suspended—is stored as a correction value.

The controller 517 constitutes corrector. More specifically, when the impedance Z existing between the first and second electrodes 501, 502 is to be measured with the measurement signal being generated by the signal generator 503, the level value of the detection signal 651 output from the rectifier circuit 508 is corrected by use of a stored correction value. Further, the controller constitutes percent body fat computer for determining percent body fat from the value corrected by the corrector and the entered height and weight. In order to display computed percent body fat in an area 552 on a screen 551 of the television set 553, an infrared signal indicating the percent body fat is transmitted from the light-emitter 521.

Figure 19:
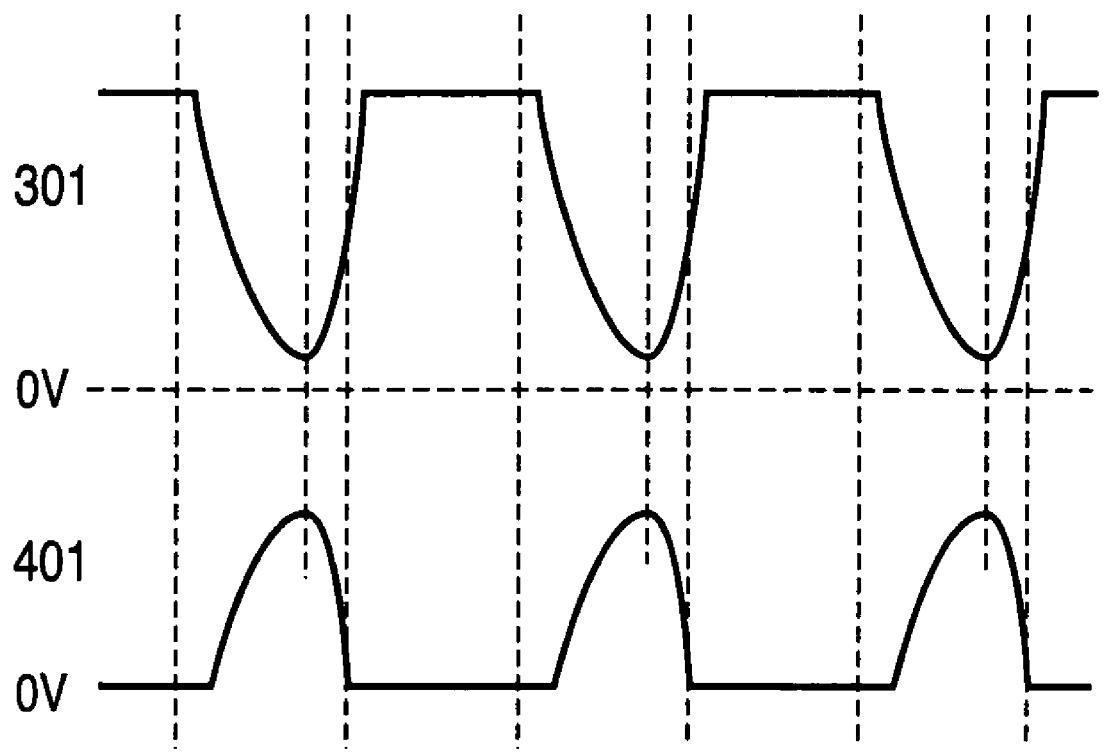
FIG. 19 is a descriptive view showing waveforms of primary signals appearing when p-n-p transistors are used as elements.

Operation for detecting the bio-impedance Z to be performed by the level detector 504 will now be described in detail. At the time of measurement of the bio-impedance Z, the control output 672 is set to a low level. Consequently, the transistor Q502 is turned off, and the resistor R506 is disconnected from the base of the p-n-p transistor Q501. Meanwhile, the pulse signal 671 is sent to the signal generator 503. Accordingly, the signal generator 503 produces a measurement signal (whose waveform is indicated by 301 in FIG. 19) and sends the thus-produced signal to the first electrode 501.

Therefore, a signal analogous to a half-wave waveform whose amplitude corresponds to the bio-impedance Z connected between the first and second electrodes 501, 502 appears on the terminal of the detection resistor R514, the terminal being connected to the second electrode 502. The signal is amplified by the p-n-p transistor Q501 and output from the collector of that transistor (the waveform of a signal output from the collector of the transistor Q501 is indicated by 401 in FIG. 19). Consequently, the level of the detection signal 651 output from the rectifier circuit 508 changes in accordance with the bio-impedance Z connected between the first and second electrodes 501, 502. The bio-impedance Z is indicated by the level value of the detection signal 651.

When transmission of the pulse signal 671 to the signal generator 503 is stopped and the signal generator 503 stops generation of a measurement signal, only a d.c. component and an extraneous noise component appear on the second electrode 502. Of these signal components, a d.c. component is interrupted by the connection capacitor C501. Further, the detection resistors R513, 514 each assume a resistance of several thousand ohms. Therefore, the impedance of the second electrode 502 with respect to the outside is low. Accordingly, in a state in which generation of the measurement signal is stopped, an extraneous noise component led to the base of the p-n-p transistor Q501 remains at a minute, negligible level even when the fingers are brought into contact with the second electrode 502.

In the above-described state, a bias current of the bias circuit 507 is set such that the collector potential of the p-n-p transistor Q501 assumes a value of about 0.7 volts. This setting is attributable to the following two reasons. The first reason is that the level value of the detection signal 651 output from the rectifier circuit 508 is brought to a value close to zero volts when no signal (i.e., the measurement signal flowing through the first electrode 501, the bio-impedance Z, and the second electrode 502) is led to the base of the p-n-p transistor Q501. The second reason is that the level value of the detection signal 651 is caused to rise when the measurement signal is led to the base of the p-n-p transistor Q501 despite the signal being of a minute level.

When the control output 672 is brought to a high level, the transistor Q502 is turned on. Consequently, the bias current set by the bias circuit 507 flows into the base of the p-n-p transistor Q501 along with the base current flowing through the resistor R506. The collector current of the p-n-p transistor Q501 is eventually increased. Consequently, even when generation of the measurement signal is suspended by the signal generator 503, the collector potential of the p-n-p transistor Q501 is increased by bringing the control output 672 to a high level. Hence, the level value of the detection signal 651 rises from a value close to zero volts to, e.g., one volt or the like.

As is described, when the temperature of the level detector 504 is increased, the base current of the p-n-p transistor Q501 is increased, thereby resulting in an increase in collector current. Accordingly, when a temperature rise arises, a rise also arises in the output level of the collector. The forward voltage of the diode D506 is decreased in accordance with the temperature rise. Hence, if a temperature rise arises even when the output level of the collector is made constant, a rise arises in the level value of the rectification output 651. Consequently, as a whole, the temperature change induces occurrence of synergistic action between an increase in the base current of the p-n-p transistor Q501 and a decrease in the forward voltage of the diode D506, thereby deteriorating a temperature characteristic.

Deterioration of the temperature characteristic arises when the level of the detection signal 651 is increased by causing the signal generator 503 to suspend generation of the measurement signal and by bringing the control output 672 to a high level (hereinafter called a "test mode"), as well as when the bio-impedance Z is detected while the signal generator 503 is caused to generate a measurement signal (hereinafter called a "measurement mode").

Under the assumption that a relationship between two types of temperatures t1, t2 is defined as (t1<t2), that the level value of the detection signal 651 obtained at the temperature t1 during the measurement mode (hereinafter called a "measurement mode level value") is taken as A, and that the level value of the detection signal 651 obtained at the temperature t1 during the test mode (hereinafter called a "test mode level value") is taken as B, at the temperature t2 the measurement mode level value assumes (A+a) and the test mode level value assumes (B+b) even when no change arises in the bio-impedance Z (a>0, b>0).

When a value C to be obtained by subtracting the test mode level value from the measurement mode level value is determined, the value C is expressed as (C=A−B) when the temperature is t1. When the temperature is t2, the value C is expressed as {C=(A+a)−(B+b)}. More specifically, the value C is expressed as {C=(A−B)+(a−b)}. This signifies that the influence of the temperature is eliminated from the subtracted value C by subtracting, from the measurement mode level value, the test mode level value obtained at the same temperature as that in the measurement mode, so long as an increment "a" attributable to a temperature rise arising during the measurement mode can be made equal to an increment "b" attributable to a temperature rise arising during the test mode.

When the increment "b" in the test mode level value resulting from a temperature rise while the test mode level value is set to one volt is compared with an increment "b" in the test mode level value resulting from a temperature while the test mode level value is set to two volts, the increment "b" obtained at a test move level value of two volts is larger. This signifies that the increment "b" resulting from a temperature rise becomes greater as the value of the resistor R506 is decreased and the bias current of the p-n-p transistor Q501 is increased. When the test mode level value is made close to zero volts, the increment "b" also becomes close to zero volts. This signifies that the best value lies in the resistor R506. A temperature change induces a change in even the level of the measurement signal to be produced by the signal generator 503. Therefore, on the basis of test results, the resistor R506 is comprehensively set to a value at which the temperature characteristic of the subtracted value C, including the temperature characteristic of the signal generator 503, becomes optimal.

As is evident from the foregoing description, when the temperature is constant, the test mode level value is constant. Accordingly, the subtracted value C changes in accordance with the bio-impedance Z connected between the first and second electrodes 501, 502. Specifically, the bio-impedance Z is indicated by the subtracted value C.

Figure 18:
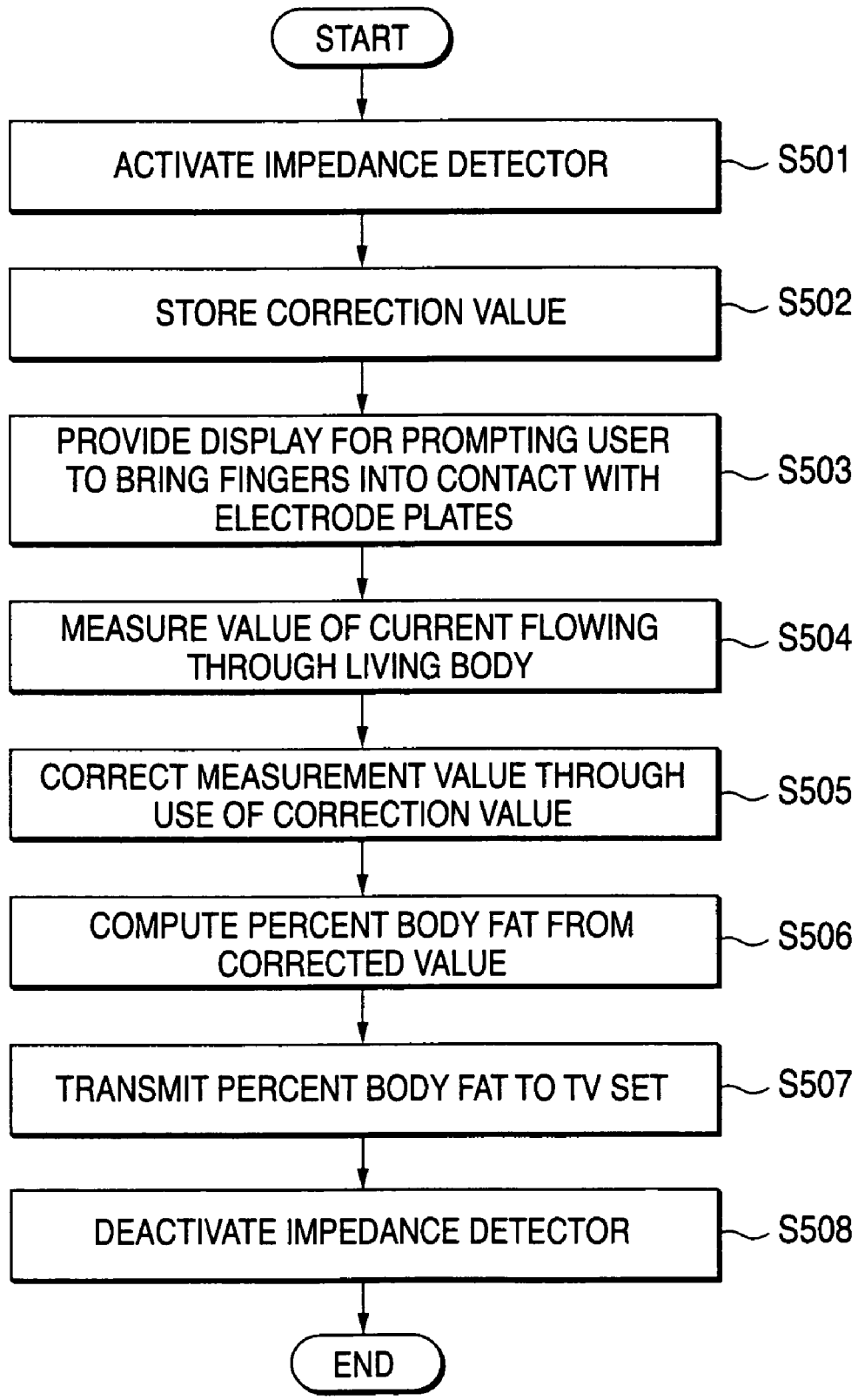
FIG. 18 is a flowchart showing the primary operation of the percent body fat measuring apparatus to be performed at the time of measurement of percent body fat.

Explanations of operation of the level detector 504 are now completed, and operation of the percent body fat measuring apparatus of the embodiment will now be described by reference to a flowchart shown in FIG. 18.

When percent body fat is not to be measured, the controller 517 brings the positive power supply P501 to zero volts, thus preventing unwanted consumption of the battery 519. It is also assumed that the weight and height of a user who attempts to measure percent body fat are already input. It is also assumed that, in this state, the user supports the main unit 531 such that an infrared ray is transmitted to the television set 553, and operates the measurement key 536, the controller 517 controls the power supply circuit 518, to thereby change the positive power supply P501 from zero volts to four volts and bring the impedance detector 515 into an operating state (step S501). The control output 672 is brought to a high level without transmission of the pulse signal 671 to the signal generator 503. At this time, the detection signal 651 output from the level detector 504 is subjected to analog-to-digital conversion, and the thus-converted value (i.e., a test mode level value) is stored as a correction value (step S502).

The controller 517 displays, on the screen 551 of the television set 553, a message for prompting the user to bring his or her left thumb into contact with the electrode plate L541, the left forefinger into contact with the electrode plate L542, the right thumb into contact with the electrode plate R541, and the right forefinger into contact with the electrode plate R542 (step S503). Generation of the measurement signal to be performed by the signal generator 503 is then commenced by transmission of the pulse signal 671 to the signal generator 503. At this time, the detection signal 651 output from the level detector 504 is subjected to analog-to-digital conversion (step S504). Next, the controller 517 corrects a measured value indicating the bio-impedance Z, by subtracting the correction value from the value determined through analog-to-digital conversion (step S505).

Next, percent body fat is computed from the corrected value and the previously-input weight and height (step S506). The thus-computed percent body fat is displayed on the screen 551 of the television set 553 (step S507). Subsequently, the voltage of the positive power supply P501 is set to zero volts by controlling the power supply circuit 518, thereby deactivating the impedance detector 515 (step S508). Consequently, the thus-measured percent body fat is displayed in the area 552 of the screen 551 of the television set 553.

A real percent body fat measuring apparatus is caused to utilize a related-art computing method at the time of computation of percent body fat from the corrected value. Hence, under the assumption that the measurement mode level value is taken A, the test mode level value is taken B, and a constant analogous to the value B is taken as K, computation is performed according to the expression {C=A+(K−B)} when the correction value C is to be determined.

By reference to FIG. 20, the configuration of the percent body fat measuring apparatus will be described when the p-n-p transistor Q501 of the level detector 504 is changed to an n-p-n transistor. Throughout the drawings, elements which are identical in operation and configuration with those shown in FIG. 16 are assigned the same reference numerals as used in FIG. 16. Therefore, an explanation is now given of only a configuration difference between the percent body fat measuring apparatus shown in FIG. 20 and that shown in FIG. 16.

Figure 16:
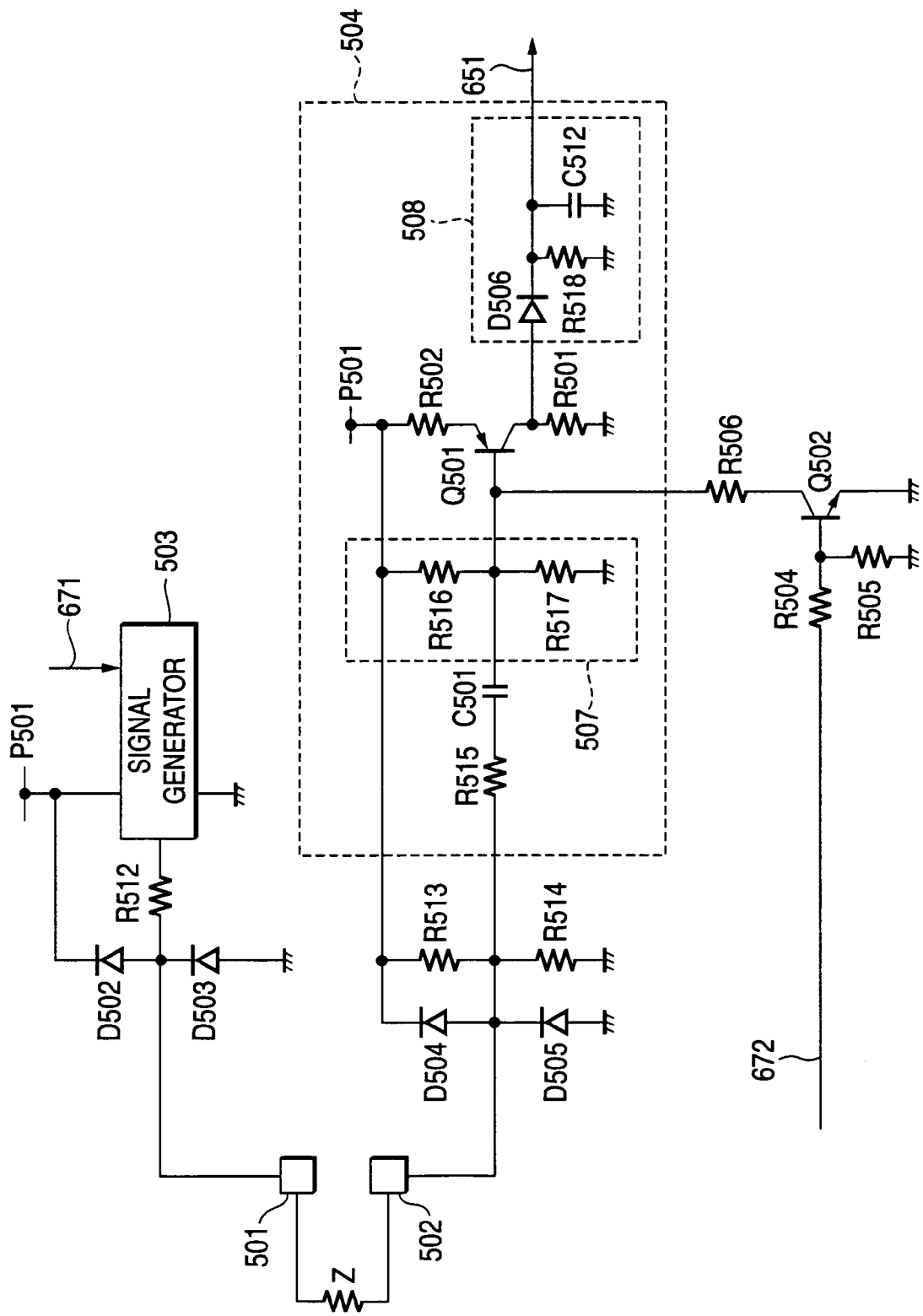
FIG. 16 is a circuit diagram showing a detailed electrical connection of impedance detector of a percent body fat measuring apparatus according to an embodiment of the invention.

The p-n-p transistor Q501 shown in FIG. 16 is changed to an n-p-n transistor Q511. In accordance with this change, the first resistor R501 is connected to the collector of the first n-p-n transistor Q511 and the positive power supply P501. Further, the second resistor R502 is connected between the emitter of the n-p-n transistor Q511 and the ground level. Further, the resistors R516, R517 in the bias circuit 507a changs their locations. The orientation of the diode D506 in a rectifier circuit 508a is changed, and the resistor R518 is connected between the anode of the diode D506 and the positive power supply P501.

A collector of a transistor Q512 is connected to the base of the n-p-n transistor Q511 by way of a resistor R509, and the emitter of the same is connected to the positive power supply P501. Further, the control output 672 of the controller 517 is led to the base of the transistor Q512 by way of the resistor R507. The transistor Q512 serves as an element for additionally imparting a bias current to the n-p-n transistor Q511 given the bias current by the bias circuit 507a, in a direction in which the output level of the rectifier circuit 508a increases (i.e., a direction approaching zero volts).

Figure 20:
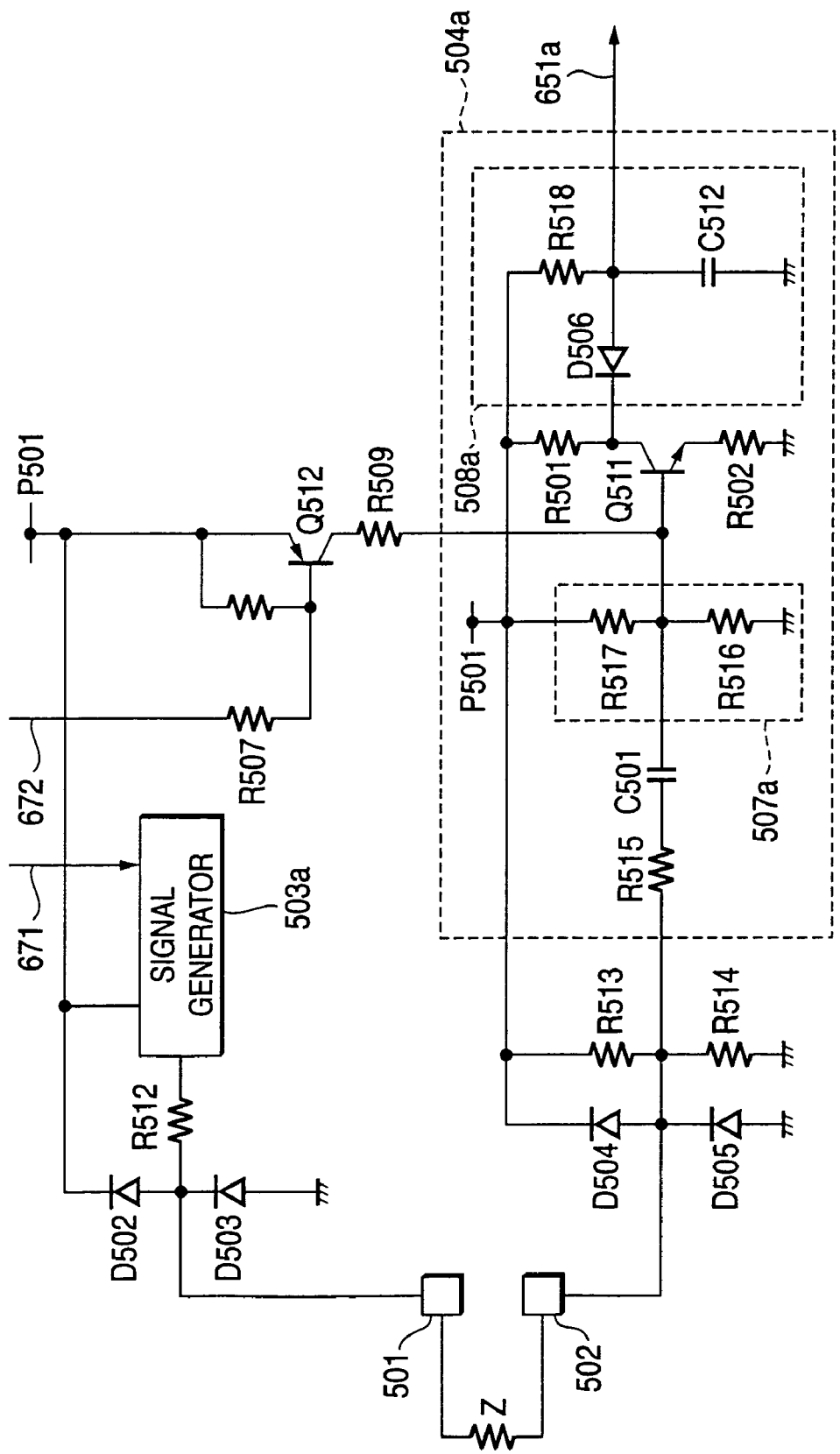
FIG. 20 is a circuit diagram showing a detailed electrical connection of impedance detector required when n-p-n transistors are used as elements.

When the level detector 504a is formed in the configuration shown in FIG. 20, the waveform of the measurement signal output from the signal generator 503a assumes a shape such that a half-wave waveform is produced in a direction in which a potential rises, as indicated by 301a in FIG. 11. Further, as indicated by 401a in FIG. 11, the waveform of the collector signal of the n-p-n transistor Q511 provided in the level detector 504a assumes a shape such that a half-wave waveform is formed in a range close to zero volts while a voltage close to four volts of the positive power supply P501 is taken as a reference potential. Accordingly, the level value of the detection signal 651a output from the rectifier circuit 508a changes so as to approximate zero volts as the value of the bio-impedance Z becomes smaller.

In a state in which generation of the measurement signal is suspended, the bias current of the bias circuit 507a is set such that the collector potential of the n-p-n transistor Q511 assumes a voltage which is lower than the positive power supply P1 by only about 0.7 volts. This setting is attributable to the following two reasons. The first reason is that the level value of a detection signal 651a output from the rectifier circuit 508a is brought to a voltage close to zero volts when no signal (i.e., the measurement signal flowing through the first electrode 501, the bio-impedance Z, and the second electrode 502) is led to the base of the n-p-n transistor Q511. The second reason is that, if the measurement signal is led to the base of the n-p-n transistor Q511, the level value of the detection signal 651a is caused to start falling even when the signal is of a minute level.

When the control output 672 is brought to a low level, the transistor Q512 is turned on. Consequently, the bias current set by the bias circuit 507a flows into the base of the n-p-n transistor Q511 in conjunction with the base current flowing through the resistor R509. Eventually, the collector current of the n-p-n transistor Q511 increases. Even when the signal generator 503 suspends generation of the measurement signal, the collector potential of the n-p-n transistor Q511 is lowered if the control output 672 is brought to a low level. Hence, the level value of the detection signal 651a falls from the voltage close to the positive power supply P501 to, e.g., three volts.

When the temperature of the level detector 504a rises, the base current of the n-p-n transistor Q511 increases, and the collector current of the same also increases. Accordingly, at the time of occurrence of a temperature rise, a drop arises in collector voltage. The forward voltage of the diode D506 decreases as a temperature rises. Even when the collector voltage is made constant, a drop will arise in the output level value of the rectification output 651a if a temperature rise arises. Therefore, as a whole, the temperature change induces occurrence of synergistic action between an increase in the base current of the n-p-n transistor Q511 and a decrease in the forward voltage of the diode D506, thereby deteriorating a temperature characteristic.

The above-described deterioration of the temperature characteristic arises when the level of the detection signal 651a is decreased by causing the signal generator 503 to suspend generation of the measurement signal and by bringing the control output 672 to a low level (hereinafter called a "test mode") as well as when the bio-impedance Z is detected while the signal generator 503 is caused to generate a measurement signal (hereinafter called a "measurement mode").

Under the assumption that a relationship between two types of temperatures t1, t2 is defined as (t1<t2), that the level value of the detection signal 651a obtained at the temperature t1 during the measurement mode (hereinafter called a "measurement mode level value") is taken as A, and that the level value of the detection signal 651a obtained at the temperature t1 during the test mode (hereinafter called a "test mode level value") is taken as B, at the temperature t2 the measurement mode level value assumes (A−a) and the test mode level value assumes (B−b) even when no change arises in the bio-impedance Z (a>0, b>0).

When a value C to be obtained by subtracting the test mode level value from the measurement mode level value is determined, the value C is expressed as (C=A−B) when the temperature is t1. When the temperature is t2, the value C is expressed as {C=(A−a)−(B−b)}. More specifically, the value C is expressed as {C=(A−B)−(a−b)}. This signifies that the influence of the temperature is eliminated from the subtracted value C by subtracting, from the measurement mode level value, the test mode level value obtained at the same temperature as that in the measurement mode, so long as an increment "a" attributable to a temperature rise arising during the measurement mode can be made equal to an increment "b" attributable to a temperature rise arising during the test mode.

When the increment "b" in the test mode level value resulting from a temperature rise while the test mode level value is set to three volts is compared with an increment "b" in the test mode level value resulting from a temperature while the test mode level value is set to two volts, the increment "b" obtained at a test move level value of two volts is larger. This signifies that the increment "b" resulting from a temperature rise becomes greater as the value of the resistor R506 is decreased and the bias current of the n-p-n transistor Q511 is increased. When the test mode level value is made close to the positive power supply P501, the increment "b" also becomes close to zero volts. This signifies that the best value lies in the resistor R509. A temperature change induces a change in even the level of the measurement signal to be produced by the signal generator 503. Therefore, on the basis of test results, the resistor R509 is comprehensively set to a value at which the temperature characteristic of the subtracted value C, including the temperature characteristic of the signal generator 503, becomes optimal.

Operation for measuring percent body fat to be performed by use of the level detector 504a having the foregoing configuration is identical with the operation for measuring percent body fat using the level detector 504 shown in FIG. 16. Hence, its explanation is omitted.

The invention is not limited to the embodiment. The embodiment describes a configuration in which acquisition of a test mode level value (i.e., a correction value) is followed by acquisition of a measurement mode level value (i.e., a level value indicating the bio-impedance Z). However, the invention can be configured such that acquisition of a measurement mode level value is followed by acquisition of a test mode level value.

In relation to the configuration shown in FIG. 16 and the configuration shown in FIG. 20, the method for correcting the measurement mode level value A is corrected through use of the test mode level value B is described by reference to the method of subtracting the test mode level value from the measurement mode level value. However, a method employing, e.g., {C=A−α×B}, can also be used as another method for correcting the measurement mode level value. Alternatively, the measurement mode level value can be divided into a plurality of ranges, such as two ranges, and the value can be corrected by changing α on a per-range basis.

The method for displaying percent body fat is described by reference to a case where percent body fat is displayed on the screen 551 of the TV set 553 which is an object of remote control. However, the function of the remote controller can be omitted, and another display device such as an LCD can be added to the percent body fat measuring apparatus. Percent body fat can be displayed on the thus-added display.

As is described, according to the invention, a measurement signal produced by the signal generator is made analogous to a half-wave waveform. The level detector detects the level of a waveform analogous to a half-wave of the signal to be detected. The signal generator has pulse generator for generating a pulse signal indicating the cycle of the measurement signal; a first resistor of which one terminal is connected to an output terminal of the pulse generator; a second resistor of which one terminal is connected to the other terminal of the first resistor; a first p-n-p transistor of which base is connected to the other terminal of the second resistor, of which collector is grounded, and of which emitter is connected to a positive power supply via a third resistor; a first capacitor of which one terminal is connected to a node between the first and second resistors and of which other terminal is connected to the emitter of the first p-n-p transistor; and a second capacitor connected between a base of the first p-n-p transistor and a ground level. The level detector has a third capacitor of which one terminal is connected to a second electrode; a second p-n-p transistor of which base is connected to the other terminal of the third capacitor, of which collector is grounded via a fourth resistor, and of which emitter is connected to the positive power supply via a fifth resistor; a bias circuit for supplying a bias current to the base of the second p-n-p transistor; and a rectifier circuit for rectifying an output from a collector of the second p-n-p transistor. The pulse generator has original pulse generator which is formed from a microcomputer and produces an original pulse signal indicating the cycle of the measurement signal; a sixth resistor of which one terminal is connected to the positive power supply; and a switching element of which one terminal is connected to the other terminal of the sixth resistor, of which other terminal is grounded, and whose connection is controlled by the original pulse signal. Further, a node between the sixth resistor and the switching element is taken as a terminal for outputting the pulse signal. Accordingly, as in the case of use of a sinusoidal waveform, the level of a rectified signal is prevented from being reduced to one-half the amplitude of the signal before rectification. The signal generator and the bias circuit are each formed from a small number of elements. Even when variation arise in the voltage of operating power supplied to the microcomputer, a high-level voltage of the pulse signal to be output remains constant at all times. Therefore, measurement accuracy required for measuring the level of the signal detected through use of electrodes can be enhanced. Further, generation of a measurement signal analogous to a half-wave waveform and conversion of the signal detected through use of electrodes into a d.c. signal can be performed through use of a simple circuit configuration and without use of an operational amplifier whose equivalent circuit configuration is complicated. Even when variations arise in the power voltage of the microcomputer which produces a pulse signal indicating the cycle of the measurement signal, occurrence of a variation in the waveform of the measurement signal can be prevented.

According to the invention, the measurement signal produced by the signal generator is made analogous to a half-wave waveform. The level detector detects the level of a waveform analogous to a half-wave of a signal to be detected. Therefore, the level detected by the level detector is substantially equal to the amplitude of a signal before rectification. As in the case of use of a sinusoidal waveform, the level of a rectified signal is prevented from being reduced to one-half the amplitude of the signal before rectification. Hence, the measurement accuracy required for measuring the level of the signal detected through use of electrodes can be enhanced.

Further, the signal generator also has;

pulse generator for generating a pulse signal indicating the cycle of the measurement signal, a first resistor of which one terminal is connected to an output terminal of the pulse generator, a second resistor of which one terminal is connected to the other terminal of the first resistor, a first p-n-p transistor of which base is connected to the other terminal of the second resistor, of which collector is grounded, and of which emitter is connected to a positive power supply via a third resistor, a first capacitor of which one terminal is connected to a node between the first and second resistors and of which other terminal is connected to the emitter of the first p-n-p transistor, and a second capacitor connected between the base of the first p-n-p transistor and a ground level. Accordingly, a waveform analogous to a half-wave waveform appears on the emitter of the first p-n-p transistor during durations before and after a rising edge of a pulse signal. The signal generator for producing a half-wave waveform is formed from a small number of elements other than the pulse generator; that is, three resistors, two capacitors, and one p-n-p transistor. Consequently, generation of a measurement signal analogous to a half-wave waveform can be performed through use of a simplified circuit configuration and without use of an operational amplifier whose equivalent circuit configuration is complicated.

The level detector also has;

a third capacitor of which one terminal is connected to a second electrode, a second p-n-p transistor of which base is connected to the other terminal of the third capacitor, of which collector is grounded via a fourth resistor, and of which emitter is connected to the positive power supply via a fifth resistor, a bias circuit for supplying a bias current to the base of the second p-n-p transistor, and a rectifier circuit for rectifying an output from the collector of the second p-n-p transistor. Accordingly, the level detector can be formed from a small number of elements; that is, five resistors, two capacitors, one p-n-p transistor, and one diode. Consequently, the signal detected through use of the electrodes can be converted into a d.c. signal through use of a simplified circuit configuration and without use of an operational amplifier whose equivalent circuit configuration is complicated.

In addition, the signal generator also has;

pulse generator for generating a pulse signal indicating the cycle of the measurement signal, a first resistor of which one terminal is connected to an output terminal of the pulse generator, a second resistor of which one terminal is connected to the other terminal of the first resistor, a first n-p-n transistor of which base is connected to the other terminal of the second resistor, of which collector is connected to a positive power supply, and of which emitter is grounded via a third resistor, a first capacitor of which one terminal is connected to a node between the first and second resistors and of which other terminal is connected to an emitter of the first n-p-n transistor, and a second capacitor connected between a base of the first n-p-n transistor and a ground level. Accordingly, a waveform analogous to a half-wave waveform appears on the emitter of the first n-p-n transistor during predetermined durations before and after a rising edge of a pulse signal. The signal generator for producing a half-wave waveform is formed from a small number of elements other than the pulse generator; that is, three resistors, two capacitors, and one n-p-n transistor. Consequently, generation of a measurement signal analogous to a half-wave waveform can be performed through use of a simplified circuit configuration and without use of an operational amplifier whose equivalent circuit configuration is complicated.

The level detector has;

a third capacitor of which one terminal is connected to the second electrode, a second n-p-n transistor of which base is connected to the other terminal of the third capacitor, of which collector is connected to the positive power supply via a fourth resistor, and of which emitter is grounded via a fifth resistor, a bias circuit for supplying a bias current to the base of the second n-p-n transistor, and a rectifier circuit for rectifying an output from the collector of the second n-p-n transistor. Accordingly, the level detector can be formed from a small number of elements; that is, five resistors, two capacitors, one n-p-n transistor, and one diode. Consequently, the signal detected through use of the electrodes can be converted into a d.c. signal through use of a simplified circuit configuration and without use of an operational amplifier whose equivalent circuit configuration is complicated.

The pulse generator has;

original pulse generator which is formed from a microcomputer and produces an original pulse signal indicating the cycle of the measurement signal, sixth resistor of which one terminal is connected to the positive power supply, and a switching element of which one terminal is connected to the other terminal of the sixth resistor, of which other terminal is grounded, and whose connection is controlled by an original pulse signal, and wherein a node between the sixth resistor and the switching element is taken as a terminal for outputting the pulse signal. Even when variations arise in the voltage of operating power to be supplied to the microcomputer, the high-level voltage of a pulse signal to be output remains constant at all times. Even when changes have arisen in the voltage of operating power to be supplied to the microcomputer, the high-level voltage of the pulse signal to be output remains constant at all times. Therefore, even when variations arise in the power voltage of the microcomputer which produces a pulse signal indicating the cycle of the measurement signal, occurrence of a variation in the waveform of the measurement signal can be prevented.

Further, as is described, according to the invention, a percent body fat measuring apparatus is provided with corrector. A level value of a detection signal is output from a rectifier circuit when a living body comes into contact with first and second electrodes while a measurement signal is being produced. Another level value of the detection signal is obtained by additionally imparting, to a p-n-p transistor given a bias current by a bias circuit, an additional bias current for shifting the level value of the detection signal while generation of the measurement signal is suspended. The corrector subtracts the latter level value from the former level value. Percent body fat computer determines percent body fat on the basis of a result of subtraction performed by the corrector. Specifically, percent body fat is determined on the basis of a measurement value whose error due to a temperature characteristic is corrected. An arithmetic operation required for effecting correction is subtraction. Therefore, deterioration of measurement accuracy of percent body fat, which would otherwise be caused by a temperature change, can be prevented, and a program required for effecting correction operation can be simplified.

Further, according to the invention, a percent body fat measuring apparatus is provided with corrector. A level value of a detection signal is output from a rectifier circuit when a living body comes into contact with first and second electrodes while a measurement signal is being produced. Another level value of the detection signal is obtained by additionally imparting, to a p-n-p transistor given a bias current by a bias circuit, an additional bias current for shifting the level value of the detection signal while generation of the measurement signal is suspended. The corrector subtracts the latter level value from the former level value. Percent body fat computer determines percent body fat on the basis of a result of subtraction performed by the corrector. Specifically, percent body fat is determined on the basis of a measurement value whose error attributable to a temperature characteristic is corrected. Hence, deterioration of measurement accuracy of percent body fat, which would otherwise be caused by a temperature change, can be prevented.

Moreover, according to the invention, a percent body fat measuring apparatus is provided with corrector. A level value of a detection signal is output from a rectifier circuit when a living body comes into contact with first and second electrodes while a measurement signal is being produced. Another level value of the detection signal is obtained by additionally imparting, to an n-p-n transistor given a bias current by a bias circuit, an additional bias current for shifting the level value of the detection signal while generation of the measurement signal is suspended. The corrector subtracts the latter level value from the former level value. Percent body fat computer determines percent body fat on the basis of a result of subtraction performed by the corrector. Specifically, percent body fat is determined on the basis of a measurement value whose error attributable to a temperature characteristic is corrected. An arithmetic operation required for effecting correction is subtraction. Therefore, deterioration of measurement accuracy of percent body fat, which would otherwise be caused by a temperature change, can be prevented, and a program required for effecting correction operation can be simplified.

According to the invention, a percent body fat measuring apparatus is provided with corrector. A level value of a detection signal is output from a rectifier circuit when a living body comes into contact with first and second electrodes while a measurement signal is being produced. Another level value of the detection signal is obtained by additionally imparting, to an n-p-n transistor given a bias current by a bias circuit, an additional bias current for shifting the level value of the detection signal while generation of the measurement signal is suspended. The corrector subtracts the latter level value from the former level value. Percent body fat computer determines percent body fat on the basis of a result of subtraction performed by the corrector. Specifically, percent body fat is determined on the basis of a measurement value whose error attributable to a temperature characteristic is corrected. Therefore, deterioration of measurement accuracy of percent body fat, which would otherwise be caused by a temperature change, can be prevented.

What is claimed is:

1. A percent body fat measuring apparatus comprising:
   first and second electrodes with which a living body is brought into contact;
   a detection resistor of which one terminal is connected to the second electrode;
   a signal generator which produces a measurement signal and applies a produced measurement signal between the first electrode and the other terminal of the detection resistor;
   a level detector for detecting the level of a signal which develops between the terminals of the detection resistor and is an object of detection; and
   a percent body fat computer for determining percent body fat on the basis of a result of detection operation performed by the level detector,
   wherein a measurement signal produced by the signal generator is analogous to a half-wave waveform;
   wherein the level detector detects the level of a waveform analogous to a half-wave of the signal to be detected;
   wherein the signal generator includes;
      a pulse generator for generating a pulse signal indicating the cycle of the measurement signal,
      a first resistor of which one terminal is connected to an output terminal of the pulse generator,
      a second resistor of which one terminal is connected to the other terminal of the first resistor,
      a first p-n-p transistor of which base is connected to the other terminal of the second resistor, of which collector is grounded, and of which emitter is connected to a positive power supply via a third resistor,
      a first capacitor of which one terminal is connected to a node between the first and the second resistors and of which other terminal is connected to the emitter of the first p-n-p transistor, and
      a second capacitor connected between a base of the first p-n-p transistor and a ground level;
   wherein the level detector includes:
      a third capacitor of which one terminal is connected to the second electrode,
      a second p-n-p transistor of which base is connected to the other terminal of the third capacitor, of which collector is grounded via a fourth resistor, and of which emitter is connected to the positive power supply via a fifth resistor,
      a bias circuit for supplying a bias current to the base of the second p-n-p transistor, and a rectifier circuit for rectifying an output from the collector of the second p-n-p transistor;

wherein the pulse generator includes:
an original pulse generator which is formed from a microcomputer and produces the original pulse signal indicating the cycle of the measurement signal,
a sixth resistor of which one terminal is connected to the positive power supply, and
a switching element of which one terminal is connected to the other terminal of the sixth resistor, of which other terminal is grounded, and of which connection is controlled by an original pulse signal;
wherein a node between the sixth resistor and the switching element is a terminal for outputting the pulse signal.

2. A percent body fat measuring apparatus comprising:
first and second electrodes with which a living body is brought into contact;
a detection resistor of which one terminal is connected to the second electrode;
a signal generator which produces a measurement signal and applies a produced measurement signal between the first electrode and the other terminal of the detection resistor;
a level detector for detecting the level of a signal which develops between the terminals of the detection resistor and is an object of detection; and
a percent body fat computer for determining percent body fat on the basis of a result of detection operation performed by the level detector,
wherein a measurement signal produced by the signal generator is analogous to a half-wave waveform; and
wherein the level detector detects the level of a waveform analogous to a half-wave of the signal to be detected;
wherein the signal generator includes:
a pulse generator for generating a pulse signal indicating the cycle of the measurement signal,
a first resistor of which one terminal is connected to an output terminal of the pulse generator,
a second resistor of which one terminal is connected to the other terminal of the first resistor,
a first p-n-p transistor of which base is connected to the other terminal of the second resistor, of which collector is grounded, and of which emitter is connected to a positive power supply via a third resistor,
a first capacitor of which one terminal is connected to a node between the first and second resistors and of which other terminal is connected to the emitter of the first p-n-p transistor, and
a second capacitor connected between the base of the first p-n-p transistor and a ground level.

3. The percent body fat measuring apparatus according to claim 2, wherein the level detector includes:
a third capacitor of which one terminal is connected to the second electrode,
a second p-n-p transistor of which base is connected to the other terminal of the third capacitor, of which collector is grounded via a fourth resistor, and of which emitter is connected to the positive power supply via a fifth resistor,
a bias circuit for supplying a bias current to the base of the second p-n-p transistor, and
a rectifier circuit for rectifying an output from the collector of the second p-n-p transistor.

4. A percent body fat measuring apparatus comprising:
first and second electrodes with which a living body is brought into contact;
a detection resistor of which one terminal is connected to the second electrode;
a signal generator which produces a measurement signal and applies a produced measurement signal between the first electrode and the other terminal of the detection resistor;
a level detector for detecting the level of a signal which develops between the terminals of the detection resistor and is an object of detection; and
a percent body fat computer for determining percent body fat on the basis of a result of detection operation performed by the level detector,
wherein a measurement signal produced by the signal generator is analogous to a half-wave waveform; and
wherein the level detector detects the level of a waveform analogous to a half-wave of the signal to be detected;
wherein the signal generator includes:
a pulse generator for generating a pulse signal indicating the cycle of the measurement signal,
a first resistor of which one terminal is connected to an output terminal of the pulse generator,
a second resistor of which one terminal is connected to the other terminal of the first resistor,
a first n-p-n transistor of which base is connected to the other terminal of the second resistor, of which collector is connected to a positive power supply, and of which emitter is grounded via a third resistor,
a first capacitor of which one terminal is connected to a node between the first and second resistors and of which other terminal is connected to an emitter of the first n-p-n transistor, and
a second capacitor connected between a base of the first n-p-n transistor and a ground level.

5. The percent body fat measuring apparatus according to claim 4, wherein the level detector includes:
a third capacitor of which one terminal is connected to the second electrode,
a second n-p-n transistor of which base is connected to the other terminal of the third capacitor, of which collector is connected to the positive power supply via a fourth resistor, and of which emitter is grounded via a fifth resistor,
a bias circuit for supplying a bias current to the base of the second n-p-n transistor, and
a rectifier circuit for rectifying an output from the collector of the second n-p-n transistor.

6. The percent body fat measuring apparatus according to claim 4, wherein the pulse generator includes:
an original pulse generator which is formed from a microcomputer and produces an original pulse signal indicating the cycle of the measurement signal,
a sixth resistor of which one terminal is connected to the positive power supply, and
a switching element of which one terminal is connected to the other terminal of the sixth resistor, of which other terminal is grounded, and of which connection is controlled by an original pulse signal,
wherein a node between the sixth resistor and the switching element is a terminal for outputting the pulse signal.

7. A percent body fat measuring apparatus comprising:
first and second electrodes, with which a living body is brought into contact;
a detection resistor, of which a first terminal is connected to the second electrode;

a signal generator which produces a measurement signal in a form of a waveform that is analogous to a half-wave waveform and applies a produced measurement signal between the first electrode and a second terminal of the detection resistor;

a level detector. which detects the level of a waveform analogous to a half-wave of a signal developing between the terminals of the detection resistor and outputs a result of detection as a detection signal;

a percent body fat computer for determining percent body fat on the basis of a level of the detection signal, the level detector including:
  a connection capacitor, of which a first terminal is connected to the second electrode,
  a p-n-p transistor, of which a base is connected to a second terminal of the connection capacitor, of which a collector is grounded via a first resistor, and of which an emitter is connected to a positive power supply via a second resistor,
  a bias circuit for supplying a bias current to the base of the p-n-p transistor, and
  a rectifier circuit which rectifies an output from the collector of the p-n-p transistor and outputs a rectified output as the detection signal; and a corrector for subtracting a correction level value of the detection signal from an output level value of the detection signal, wherein the correction level value is equivalent to a level value of the detection signal obtained by imparting an additional bias current to the p-n-p transistor while generation of the measurement signal is suspended, wherein the output level value is equivalent to an output from the rectifier circuit when the living body comes into contact with the first and second electrodes while a measurement signal is produced;

wherein the percent body fat computer determines percent body fat based on a result of correction performed by the corrector.

8. A percent body fat measuring apparatus comprising:
first and second electrodes, with which a living body is brought into contact;
a detection resistor, of which a first terminal is connected to the second electrode;
a signal generator which produces a measurement signal whose waveform is analogous to a half-wave waveform and applies a produced measurement signal between the first electrode and a second terminal of the detection resistor;
a level detector which detects the level of a waveform analogous to a half-wave of a signal developing between the terminals of the detection resistor and outputs a result of detection as a detection signal; and
a percent body fat computer for determining percent body fat on the basis of a level value of the detection signal;
the level detector including:
  a connection capacitor, of which a first terminal is connected to the second electrode,
  a p-n-p transistor, of which a base is connected to a second terminal of the connection capacitor, of which a collector is grounded via a first resistor, and of which an emitter is connected to a positive power supply via a second resistor,
  a bias circuit for supplying a bias current to the base of the p-n-p transistor, and
  a rectifier circuit which rectifies an output from the collector of the p-n-p transistor and outputs a rectified output as the detection signal;

a corrector for correcting an output level value of the detection signal with a correction level value, wherein the output level value is output from the rectifier circuit when a living body comes into contact with the first and second electrodes while a measurement signal is produced, and wherein the correction level value is equivalent to a level value of the detection signal obtained by imparting an additional bias current to the p-n-p transistor while generation of the measurement signal is suspended, wherein the percent body fat computation determines percent body fat based on a result of correction performed by the corrector.

9. A percent body fat measuring apparatus comprising:
first and second electrodes, with which a living body is brought into contact;
a detection resistor, of which a first terminal is connected to the second electrode;
a signal generator which produces a measurement signal in a form of a waveform that is analogous to a half-wave waveform and applies a produced measurement signal between the first electrode and a second terminal of the detection resistor;
a level detector which detects the level of a waveform analogous to a half-wave of a signal developing between the terminals of the detection resistor and outputs a result of detection as a detection signal; and
a percent body fat computer for determining percent body fat on the basis of a level value of the detection signal;
the level detector including:
  a connection capacitor, of which a first terminal is connected to the second electrode,
  an n-p-n transistor, of which a base is connected to a second terminal of the connection capacitor, of which a collector is connected to a positive power supply via a first resistor, and of which an emitter is grounded via a second resistor,
  a bias circuit for supplying a bias current to the base of the n-p-n transistor, and
  a rectifier circuit which rectifies an output from the collector of the n-p-n transistor;

a corrector for subtracting a correction level value of the detection signal from an output level value of the detection signal, wherein the correction level value is equivalent to a level value of the detection signal obtained by imparting an additional bias current to the n-p-n transistor while generation of the measurement signal is suspended, wherein the output level value is equivalent to an output from the rectifier circuit when the living body comes into contact with the first and second electrodes while a measurement signal is produced;

wherein the percent body fat computer determines percent body fat based on a result of correction performed by the corrector.

10. A percent body fat measuring apparatus comprising:
first and second electrodes, with which a living body is brought into contact;
a detection resistor, of which a first terminal is connected to the second electrode;
a signal generator which produces a measurement signal of which waveform is analogous to a half-wave waveform and applies a produced measurement signal between the first electrode and a second terminal of the detection resistor;
a level detector which detects the level of a waveform analogous to a half-wave of a signal developing between the terminals of the detection resistor and outputs a result of detection as a detection signal; and a percent body fat computer for determining percent body fat on the basis of a level value of the detection signal;

the level detector including:
- a connection capacitor, of which a first terminal is connected to the second electrode,
- an n-p-n transistor, of which a base is connected to a second terminal of the connection capacitor, of which a collector is connected to a positive power supply via a first resistor, and of which an emitter is grounded via a second resistor,
- a bias circuit for supplying a bias current to the base of the n-p-n transistor, and
- a rectifier circuit which rectifies an output from the collector of the n-p-n transistor;
- a corrector for correcting an output level value of the detection signal with a correction level value, wherein the output level value is output from the rectifier circuit when a living body comes into contact with the first and second electrodes while a measurement signal is produced, and wherein the correction level value is equivalent to a level value of the detection signal obtained by imparting an additional bias current to the n-p-n transistor while generation of the measurement signal is suspended, wherein the percent body fat computer determines percent body fat based on a result of correction performed by the corrector.

* * * * *